United States Patent [19]

Takehiko et al.

[11] Patent Number: 5,463,073
[45] Date of Patent: Oct. 31, 1995

[54] THIENOIMIDAZOLE DERIVATIVES, THEIR PRODUCTION AND USE

[75] Inventors: Naka Takehiko, Kobe; Inada Yoshiyuki, Kawanishi, both of Japan

[73] Assignee: Takeda Chemical Industries, Ltd., Osaka, Japan

[21] Appl. No.: 112,793

[22] Filed: Aug. 27, 1993

Related U.S. Application Data

[63] Continuation of Ser. No. 782,549, Oct. 25, 1991, abandoned.

[30] Foreign Application Priority Data

Oct. 30, 1990 [JP] Japan ..................... 2-294655
Apr. 23, 1991 [JP] Japan ..................... 3-092081
Jun. 21, 1991 [JP] Japan ..................... 3-150643

[51] Int. Cl.$^6$ ........................ A61K 31/415; C07D 235/02
[52] U.S. Cl. ............................ 548/303.7; 514/393
[58] Field of Search ..................... 548/303.7; 514/393

[56] References Cited

U.S. PATENT DOCUMENTS

| | | | |
|---|---|---|---|
| 4,880,804 | 11/1989 | Carini et al. | 514/234.5 |
| 5,338,756 | 8/1994 | Fortin et al. | 514/394 |

FOREIGN PATENT DOCUMENTS

| | | |
|---|---|---|
| 0028834 | 5/1981 | European Pat. Off. . |
| 0245637 | 11/1987 | European Pat. Off. . |
| 0253310 | 1/1988 | European Pat. Off. . |
| 0323841 | 7/1989 | European Pat. Off. . |
| 0392317 | 10/1990 | European Pat. Off. . |
| 0399732 | 11/1990 | European Pat. Off. . |
| 0400835 | 12/1990 | European Pat. Off. . |
| 0407102 | 1/1991 | European Pat. Off. . |
| 0411507 | 2/1991 | European Pat. Off. . |
| 0420237 | 4/1991 | European Pat. Off. . |

*Primary Examiner*—David B. Springer
*Attorney, Agent, or Firm*—Foley & Lardner

[57] ABSTRACT

Benzimidazole derivatives of the formula (I):

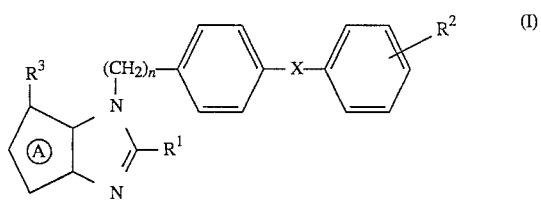

wherein the ring A is a thiophene ring which may optionally contain substitution in addition to the $R^3$ group; $R^1$ is hydrogen or an optionally substituted hydrocarbon residue which may be bonded through a heteroatom; $R^2$ and $R^3$ are independently a group capable of forming an anion or a group convertible thereinto; X is a direct bond or a spacer having an atomic length of two or less between the phenylene group and the phenyl group; and n is an integer of 1 or 2; or a salt thereof, have potent angiotensin II antagonistic activity and antihypertensive activity, thus being useful as therapeutic agents for treating circulatory system diseases such as hypertensive diseases, heart diseases (e.g. hypercardia, heart failure, cardiac infarction, etc.), strokes, cerebral apoplexy, nephritis, etc.

20 Claims, No Drawings

THIENOIMIDAZOLE DERIVATIVES, THEIR PRODUCTION AND USE

This application is a continuation of U.S. application Ser. No. 07/782,549, filed Oct. 25, 1991, now abandoned.

FIELD OF THE INVENTION

This invention relates to novel thienoimidazole derivatives having potent pharmacological actions and intermediates for the synthesis thereof.

More particularly, the present invention relates to compounds represented by the general formula (I):

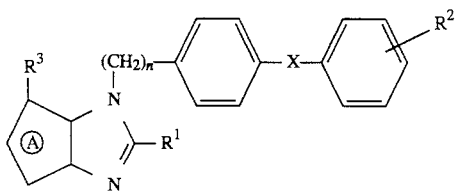

wherein the ring A is a thiophene ring which may optionally contain substitution in addition to the $R^3$ group; $R^1$ is hydrogen or an optionally substituted hydrocarbon residue which may be bonded through a hetero atom; $R^2$ and $R^3$ are independently a group capable of forming an anion or a group convertible thereinto; X is a direct bond or a spacer having an atomic length of two or less between the phenylene group and the phenyl group; and n is an integer of 1 or 2] or salts thereof, having strong angiotensin II antagonistic activity and potent anti-hypertensive activity, which are useful as therapeutic agents for treating circulatory diseases such as hypertensive diseases, heart diseases (e.g. hypercardia, heart failure, cardiac infarction, etc.), cerebral apoplexy, nephritis with proteinuria, arteriosclerosis, etc.

BACKGROUND OF THE INVENTION

The renin-angiotensin system is involved in the homeostatic function to control systemic blood pressure, the volume of body fluid, balance among the electrolytes, etc., associated with the aldosterone system. Development of angiotensin II converting enzyme inhibitors (ACE inhibitor) (this converting enzyme produces angiotensin II which possesses a strong vasoconstrictive action) has clarified the relation between the renin-angiotensin system and hypertension. Since angiotensin II constricts a blood vessel to elevate blood pressure via the angiotensin II receptors on the cellular membranes, angiotensin II antagonists, like the ACE inhibitor, would be useful in treating hypertension caused by angiotensin. It has been reported that various angiotensin II analogues such as saralasin, [$Sar^1$, $Ala^8$]AII, and the like, possess potent angiotensin II antagonist activity. It has, however, been reported that, when peptide antagonists are administered parenterally, their actions are not prolonged and, when administered orally, they are ineffective [M. A. Ondetti and D. W. Cushman, Annual Reports in Medicinal Chemistry, 13, 82–91(1978)].

On the other hand, for solving the problems observed with these peptide antagonists, studies on non-peptide angiotensin II antagonists have been - conducted. In the earliest studies in this field, imidazole derivatives having angiotensin II antagonist activity have been disclosed in Japanese Patent Unexamined Publication Nos. 71073/1981, 71074/1981, 92270/1982, and 15768/1983, U.S. Pat. Nos. 4,355, 040 and 4,340,598, etc. Later, improved imidazole derivatives were disclosed in EP-0253310, EP-0291969, EP-0324377, and Japanese Patent Unexamined Publication No. 23868/1988 and Japanese Patent Unexamined Publication No. 117876/1989. And, as angiotensin II antagonists, pyrrole, pyrazole and triazole derivatives are disclosed in EP-0323841 and Japanese Patent Unexamined Publication No. 287071/1989, while benzimidazole derivatives are disclosed in U.S. Pat. No. 4,880,804.

DETAILED DESCRIPTION OF THE INVENTION

The present inventors considered that compounds functioning to control resin-angiotensin system as well as clinically useful for the treatment of circulatory diseases such as hypertensive diseases, heart diseases (e.g. hypercardia, heart failure, cardiac infarction, etc.), cerebral apoplexy, etc. are required to have potent angiotensin II receptor antagonistic activity and to show a strong and long-lasting angiotensin II antagonistic and hypotensive action by oral administration, and they have diligently conducted research work on the basis of the above consideration.

As a result of this research, the present inventors have found that novel substituted thienoimidazole derivatives (I) have a potent angiotensin II receptor antagonistic activity as well as exerting strong oral and long-lasting angiotensin II antagonistic and anti-hypertensive action, and they have developed further research work to accomplish the present invention.

More specifically, the present invention relates to compounds of the formula (I):

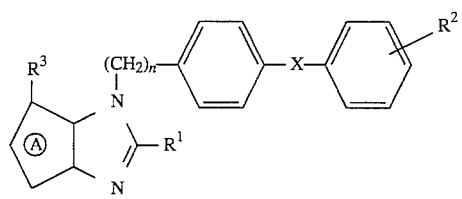

[wherein the ring A is a thiophene ring which may optionally contain substitution in addition to the $R^3$ group; $R^1$ is hydrogen or an optionally substituted hydrocarbon residue which may be bonded through a hetero atom; $R^2$ and $R^3$ are independently a group capable of forming an anion or a group convertible thereinto; X is a direct bond or a spacer having an atomic length of two or less between the phenylene group and the phenyl group; and n is an integer of 1 or 2] or salts thereof.

With regard to the foregoing general formula (I), hydrocarbon residues for $R^1$ include, for example, alkyl, alkenyl, alkynyl, cycloalkyl, aryl and aralkyl groups. Among them, alkyl, alkenyl and cycloalkyl groups are preferable.

Alkyl groups for $R^z$ are alkyl groups having 1 to about 8 carbon atoms, which may be straight or branched, and include, for example, methyl, ethyl, propyl, isopropyl, butyl, isobutyl, sec-butyl, t-butyl, pentyl, i-pentyl, hexyl, heptyl, octyl, and the like.

Alkenyl groups for $R^z$ are alkenyl groups having 2 to about 8 carbon atoms, which may be straight or branched, and include, for example, vinyl, propenyl, 2-butenyl, 3-butenyl, isobutenyl, 2-octenyl, and the like.

Alkynyl groups for $R^1$ are alkynyl groups having 2 to about 8 carbon atoms, which may be straight or branched, and include, for example, ethynyl, propynyl, butynyl, octynyl, and the like.

Cycloalkyl groups for $R^1$ are lower cycloalkyl groups having 3 to about 6 carbon atoms, and include, for example, cyclopropyl, cyclobutyl, cyclopentyl, cyclohexyl, and the like.

The above-mentioned alkyl, alkenyl, alkynyl and cycloalkyl groups may be substituted with hydroxyl, an optionally substituted amino group (e.g. amino, methylamino, $(C_{1-4})$ alkylamino, di$(C_{1-4})$ alkylamino etc.), halogen, a lower $(C_{1-4})$ alkylthio group, a lower $(C_{1-4})$ alkoxy group or the like.

Aralkyl groups for $R^1$ include, for example, phenyl-lower $(C_{1-4})$ alkyl such as benzyl, phenethyl, and the like, and the aralkyl group may be substituted with, for example, halogen (e.g. F, Cl, Br, etc.), nitro, lower $(C_{1-4})$ alkoxy (e.g. methoxy, ethoxy, etc.), lower $(C_{1-4})$ alkyl (e.g. methyl, ethyl, etc.), or the like at optional positions of the benzene ring.

Aryl groups for $R^1$ include, for example, phenyl, and the aryl group may be substituted with, for example, halogen (e.g. F, Cl, Br, etc.), nitro, lower $(C_{1-4})$ alkoxy (e.g. methoxy, ethoxy, etc.), lower $(C_{1-4})$ alkyl (e.g. methyl, ethyl, etc.), or the like at optional positions of the benzene ring.

Hydrocarbon residues for $R^1$ may be bonded to the imidazole skeleton through a hetero atom. Examples of the hetero atom include —O—, —S(O)m— [wherein m denotes 0, 1 or 2], —N($R^5$)— [wherein $R^5$ stands for hydrogen or an optionally substituted lower $(C_{1-4})$ alkyl group], preferably —O—, —S— and —NH—.

Among the above-mentioned hydrocarbon residues for $R^1$, optionally substituted lower alkyl groups having 1 to about 6 carbon atoms, which may be bonded to the imidazole ring through a hetero atom, or the like are preferable, and lower alkyl groups having 1 to about 4 carbon atoms, which are bonded to the imidazole ring through oxygen or sulfur atom, are more preferable.

Examples of groups capable of forming an anion or groups convertible thereinto for $R^2$ or $R^3$ include carboxyl, tetrazolyl, trifluoromethanesulfonic amide (—NHSO$_2$CF$_3$), phosphoric acid, sulfonic acid, cyano, lower $(C_{1-4})$ alkoxycarbonyl, and the like. These groups may be protected with, for example, an optionally substituted lower alkyl group (e.g. lower $(C_{1-4})$ alkyl, etc.) or an acyl group (e.g. lower $(C_{1-4})$ alkanoyl, optionally substituted benzoyl, etc.). Such groups may include those which are capable of forming anions or convertible thereinto either chemically or physiologically, i.e. under physiological conditions (for example, in vivo reaction such as oxidation, reduction or hydrolysis catalyzed by in vivo enzymes).

The compounds wherein $R^2$ or $R^3$ is a group capable of forming an anion or convertible thereinto chemically (e.g. by oxidation, reduction or hydrolysis) (for example, an optionally protected tetrazolyl group (e.g. a group having the formula:

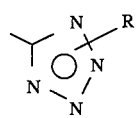

[wherein R stands for methyl, triphenylmethyl, 2-tetrahydropyranyl, methoxymethyl, ethoxymethyl or optionally substituted benzyl (e.g. p-methoxybenzyl, p-nitrobenzyl, etc.)], cyano and the like) are useful as synthetic intermediates.

Among the above-mentioned groups for $R^2$ preferred examples are tetrazolyl or carboxyl groups optionally protected with an optionally substituted lower alkyl or acyl group, and trifluoromethanesulfonic amide.

Preferable groups for $R^3$ include carboxyl groups optionally esterified or amidated (e.g. groups having the formula: —CO—D' [wherein D' is i) hydroxyl group, ii) optionally substituted amino (e.g. amino, N-lower $(C_{1-4})$ alkylamino, N,N-di-lower $(C_{1-4})$ alkylamino, etc.) or iii) optionally substituted alkoxy {e.g. a) lower $(C_{1-6})$ alkoxy group optionally whose alkyl moiety may be substituted with a hydroxyl group, optionally substituted amino (e.g. amino, dimethylamino, diethylamino, piperidino, morpholino, etc.), halogen, a lower $(C_{1-6})$ alkoxy, a lower $(C_{1-4})$ alkylthio, or optionally substituted dioxolenyl (e.g. 5-methyl-2-oxo-1,3-dioxolen-4-yl, etc.), or b) groups having the formula: —OCH($R^7$)OCOR$^8$ [wherein $R^7$ is (1) hydrogen, (2) $C_{1-6}$ straight or branched lower alkyl (e.g. methyl, ethyl, n-propyl, isopropyl, n-butyl, isobutyl, t-butyl, n-pentyl, isopentyl, neopentyl, etc.), or (3) $C_{5-7}$ cycloalkyl (e.g. cyclopentyl, cyclohexyl, cycloheptyl, etc.) and $R^8$ is (1) $C_{1-6}$ straight or branched lower alkyl (e.g. methyl, ethyl, n-propyl, isopropyl, n-butyl, isobutyl, sec-butyl, t-butyl, n-pentyl, isopentyl, neopentyl, etc.), (2) $C_{2-8}$ lower alkenyl (e.g. vinyl, propenyl, allyl, isopropenyl, etc.), (3) $C_{5-7}$ cycloalkyl (e.g. cyclopentyl, cyclohexyl, cycloheptyl, etc.), (4) $C_{1-3}$ lower alkyl (e.g. benzyl, p-chlorobenzyl, phenethyl, cyclopentylmethyl, cyclohexylmethyl, etc.), substituted with $C_{1-7}$ cycloalkyl (e.g. cyclopentyl, cyclohexyl, cycloheptyl, etc.) or aryl (e.g. phenyl, etc.), (5) $C_{2-3}$ lower alkenyl (e.g. cinnamyl, etc. such as cycloalkyl- or aryl-$C_{2-3}$alkenyl, etc. having alkenyl moiety such as vinyl, propenyl, allyl, isopropenyl, etc.), substituted with $C_{5-7}$ cycloalkyl (e.g. cyclopentyl, cyclohexyl, cycloheptyl, etc.) or aryl (e.g. phenyl, etc.), (6) aryl such as optionally substituted phenyl (e.g. phenyl, p-tolyl, naphthyl, etc.), (7) $C_{1-6}$ straight or branched lower alkoxy (e.g. methoxy, ethoxy, n-propoxy, isopropoxy, n-butoxy, isobutoxy, sec-butoxy, t-butoxy, n-pentyloxy, isopentyloxy, neopentyloxy, etc.), (8) $C_{2-8}$ straight or branched lower alkenyloxy (e.g. allyloxy, isobutenyloxy, etc.), (9) $C_{5-7}$ cycloalkyloxy (e.g. cyclopentyloxy, cyclohexyloxy, cycloheptyloxy, etc.), (10) $C_{1-3}$ lower alkoxy substituted with $C_{5-7}$ cycloalkyl (e.g. cyclopentyl, cyclohexyl, cycloheptyl, etc.) or aryl (e.g. optionally substituted phenyl, etc. [said substituted alkoxy includes cycloalkyl-or aryl-$C_{1-3}$ alkoxy having alkoxy moiety such as methoxy, ethoxy, n-propoxy, isopropoxy, etc. (e.g. benzyloxy, phenethyloxy, cyclopentylmethyloxy, cyclohexylmethyloxy, etc.)], (11) $C_{2-3}$ lower alkenyloxy substituted with $C_{5-7}$ cycloalkyl (e.g. cyclopentyl, cyclohexyl, cycloheptyl, etc.) or aryl (e.g. optionally substituted phenyl, etc.) [said substituted alkenyloxy includes cycloalkyl-or aryl-$C_{2-3}$ alkenyloxy having alkenyloxy moiety such as vinyloxy, propenyloxy, allyloxy, isopropenyloxy, etc. (e.g. cinnamyloxy, etc.)], or (12) aryloxy such as optionally substituted phenoxy (e.g. phenoxy, p-nitrophenoxy, naphthoxy, etc.)]}]) or optionally protected tetrazolyl (e.g. tetrazolyl optionally protected with alkyl (e.g. lower $(C_{1-4})$ alkyl, etc.) or acyl (e.g. lower $(C_{1-5})$ alkanoyl, optionally substituted benzoyl, etc.)). Preferable examples of substituents for $R^3$ include —COOH and salts thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-yl-methoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl, etc. Such groups may include those which are capable of forming anions (e.g. COO⁻, derivatives thereof, etc.) or convertible thereinto either chemically or physiologically i.e. under physiological conditions (for example, in vivo reaction such as oxidation, reduction or hydrolysis catalyzed by in vivo enzymes). And, $R^3$ may be carboxyl or a prodrug derivative thereof, or $R^3$ may be groups convertible into anion physiologically or chemically in vivo.

The thiophene ring A may optionally contain substitution in addition to the $R^3$ group, and example of such substituents include halogen (e.g. F, Cl, Br, etc.); nitro; cyano; optionally substituted amino [e.g. amino, N-lower ($C_{1-4}$) alkylamino (e.g. methylamino, etc.), N,N-dilower ($C_{1-4}$) alkylamino (e.g. dimethylamino, etc.), N-arylamino (e.g. phenylamino, etc.), alicyclic amino (e.g. morpholino, piperidino, piperazino, N-phenylpiperazino, etc.), etc.]; groups having the formula: —W—R6 [wherein W is a chemical bond, —O—, —S— or —C(=O)—, and $R^6$ is hydrogen or an optionally substituted lower alkyl group (e.g. a lower ($C_{1-4}$) alkoxy group optionally substituted with hydroxyl, optionally substituted amino (e.g. amino, etc.), halogen, lower ($C_{1-4}$) alkyl, etc., etc.]; groups having the formula —(CH₂)l—CO—D [wherein D is i) hydrogen, ii) hydroxyl, iii) amino, iv) N-lower ($C_{1-4}$) alkylamino, v) N,N-di-lower ($C_{1-4}$) alkylamino or vi) a lower ($C_{1-6}$) alkoxy group whose alkyl moiety is optionally substituted with a) hydroxyl, b) optionally substituted amino (e.g. amino, dimethylamino, diethylamino, piperidino, morpholino, etc.), c) halogen, d) groups having the formula: —OC($R^7$)HOCOR⁸ [wherein $R^7$ and $R^8$ are of the same meaning as defined above], e) lower ($C_{1-6}$) alkoxy, f) lower ($C_{1-6}$) alkylthio, or g) a lower ($C_{1-6}$) alkoxy group optionally substituted with optionally substituted dioxolenyl (e.g. 5-methyl-2-oxo-1,3-dioxolen-4-yl, etc.), and denotes 0 or 1]; tetrazolyl optionally protected with alkyl (e.g. lower ($C_{1-4}$) alkyl, etc.) or acyl (e.g. lower ($C_{2-5}$) alkanoyl, optionally substituted benzoyl, etc.); trifluoromethanesulfonic amide; phosphoric acid; or sulfonic acid.

X shows that the adjacent phenylene group is bonded to the phenyl group directly or through a spacer with an atomic chain of 2 or less. As the spacer, any one can be exemplified, so long as it is a divalent chain in which the number of atoms constituting the straight chain is 1 or 2, and it may have a side chain. Examples of such spacers include lower ($C_{1-4}$) alkylene, —C(O)—, —O—, —S—, —N(H)—, —C(=O)—N(H)—, —O—C(H₂)—, —S—C(H₂)—, —C(H)=C(H)—, etc.

Among the compounds represented by the above formula (I), preferable embodiments of the present invention are a compound ( I-1 ) or a compound ( I-2 ) [more preferably the compound (I-1)] having the formula:

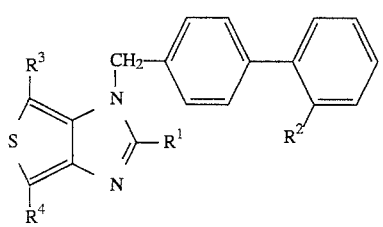

[I-1]

or

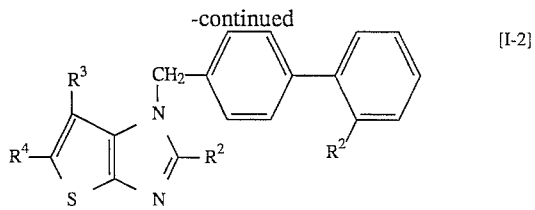

[I-2]

[wherein $R^1$ is a lower ($C_{1-6}$) alkyl group optionally bonded through a hetero atom; $R^3$ is a group of —CO—D' [wherein D' is hydroxyl, amino, N-lower ($C_{1-4}$) alkylamino, N,N-dilower ($C_{1-4}$) alkylamino or lower ($C_{1-4}$) alkoxy optionally substituted with hydroxyl, amino, halogen, lower ($C_{2-6}$) alkanoyloxy (e.g. acetyloxy, pivaloyloxy, etc.), 1-lower ($C_{1-6}$) alkoxycarbonyloxy (e.g. methoxycarbonyloxy, ethoxycarbonyloxy, cyclohexyloxycarbonyloxy, etc.) or lower ($C_{1-4}$) alkoxy on the alkyl moiety, or tetrazolyl optionally protected with a lower ($C_{1-4}$) alkyl or acyl group (e.g. lower ($C_{2-5}$) alkanoyl, benzoyl, etc.); $R^2$ is tetrazolyl or carboxyl (preferably tetrazolyl) optionally protected with an optionally substituted lower ($C_{1-4}$) alkyl (e.g. methyl, triphenylmethyl, methoxymethyl, ethoxymethyl, p-methoxybenzyl, p-nitrobenzyl, etc.) or acyl group (e.g. lower ($C_{2-5}$) alkanoyl, benzoyl, etc.); and $R^4$ is hydrogen, halogen, lower ($C_{1-4}$) alkyl, lower ($C_{1-4}$) alkoxy, nitro, a group of —CO—D" [wherein D" is hydroxyl or lower ($C_{1-2}$) alkoxy] or amino optionally substituted with lower ($C_{1-4}$) alkyl (preferably hydrogen, lower ($C_{1-4}$) alkyl, halogen, more preferably hydrogen)].

PRODUCTION METHOD

The compounds of the above-mentioned general formula (I) can be prepared by several reaction schema, as illustrated below.

Reaction (a)

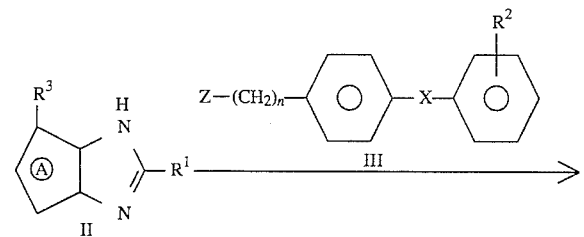

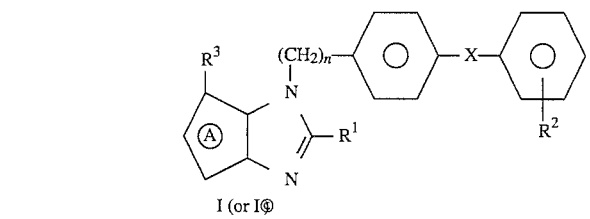

I (or I⊕)

[wherein A, $R^1$, $R^2$, $R^3$, X and n have the above-defined meanings and Z is halogen]

Reaction (b)

-continued

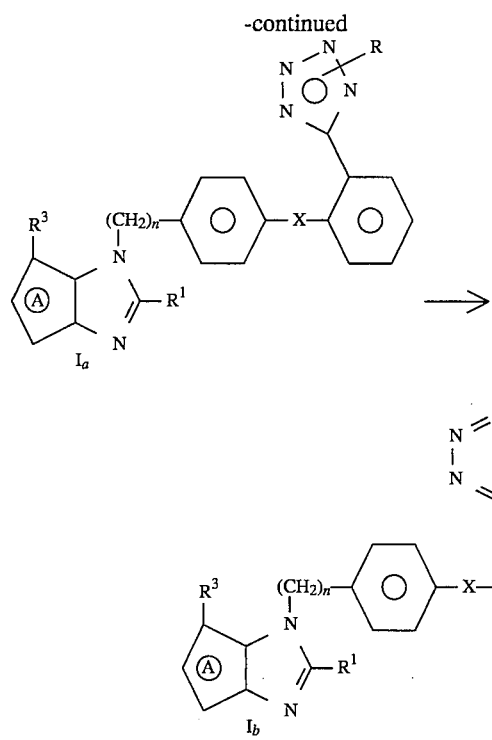

[wherein each symbol has the above-defined meaning]

Reaction (c)

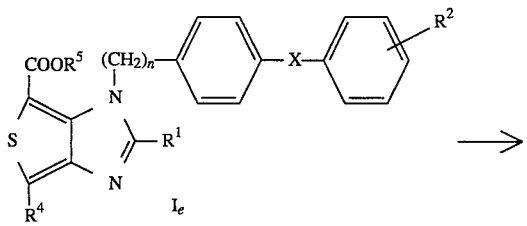

[wherein $R^1$, $R^2$, X, Z and n have the above-defined meanings]

Reaction (d)

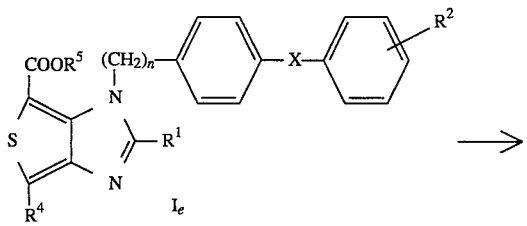

-continued

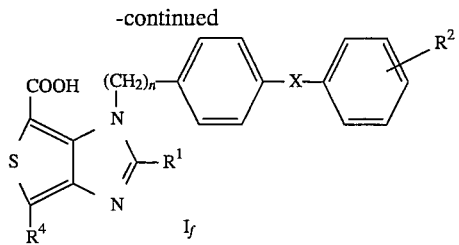

wherein $R^1$, $R^2$, $R^4$, X and n have the above-defined meanings and $R^6$ is lower alkyl]

Reaction (e)

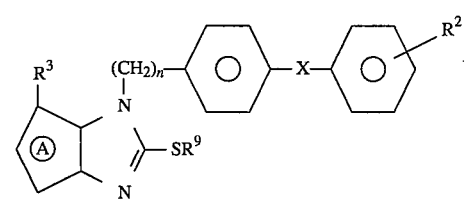

wherein $R^2$, $R^3$, A, X and n have the above-defined meanings, and $R^9$ is an optionally substituted lower hydrocarbon residue]

Reaction (f)

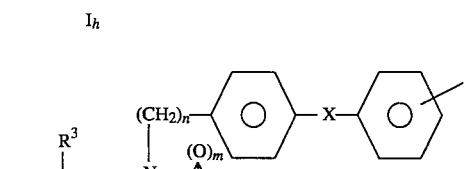

-continued

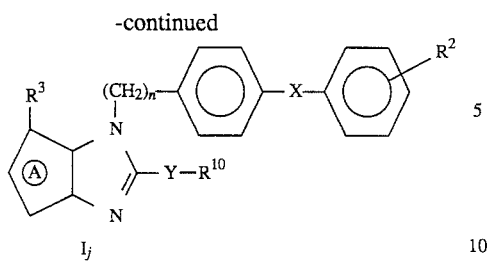

[$R^2$, $R^3$, $R^9$, A, X, Y and n have the above-defined meanings, and R10 is an optionally substituted lower hydrocarbon residue]

Reaction (g)

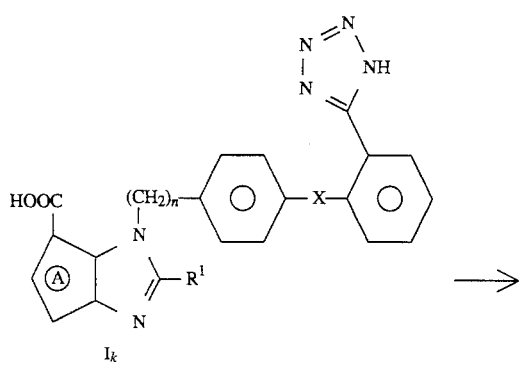

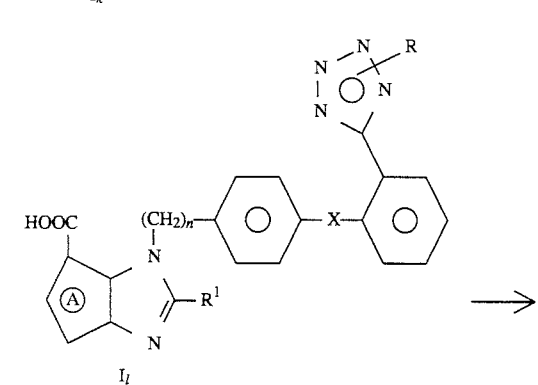

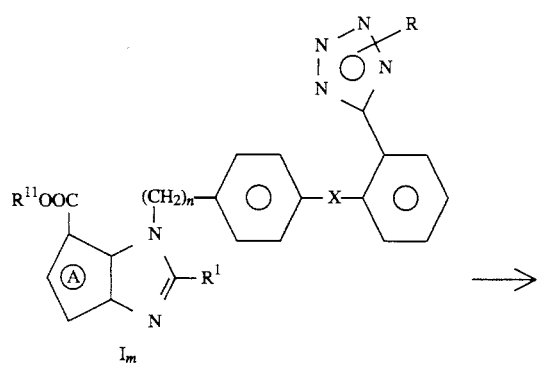

-continued

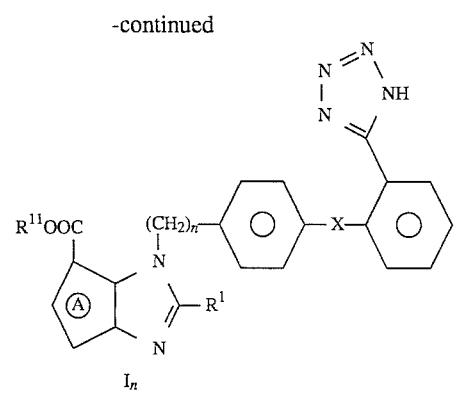

wherein $R^1$, R, A, X and n have the above-defined meanings, and $R^{11}$ is the group shown by the above-mentioned formula: —C($R^7$)HOCO$R^8$]

Reaction (h)

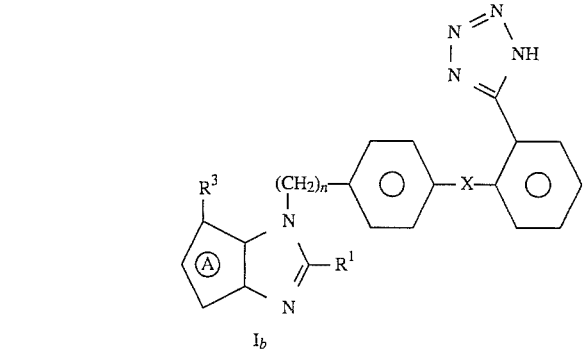

[wherein $R^1$, $R^3$, A, X and n have the above-defined meanings]

The above-illustrated reaction (a) is an alkylation using an alkylating agent in the presence of a base.

The alkylation is conducted, employing approximately 1 to 3 moles each of the base and the alkylating agent relative to one mole of the compound (II), usually in a solvent such as dimethylformamide, dimethylacetamide, dimethylsulfoxide, acetonitrile, acetone, ethylmethylketone, etc.

Examples of the base include sodium hydride, potassium t-butoxide, potassium carbonate and sodium carbonate.

As the alkylating agent, use is made of, for example, substituted halides (e.g. chlorides, bromides, iodides and the like), substituted sulfonate esters (e.g. methyl p-toluenesulfonate or the like), etc.

While the reaction conditions may vary depending on the combination of the base and the alkylating agent, it is preferable to conduct the reaction usually at 0° C. to room temperature for 1 to 10 hours.

In the said alkylation, a mixture of two isomers, (I) and (I') is usually obtained depending on the position of the N atom to be alkylated. While the production ratio of Compound (I) and Compound (I') varies with the reaction conditions then employed and the substituents on the thiophene ring, these two compounds can be obtained easily as pure products respectively by conventional isolation and purification methods (e.g. recrystallization, column chromatography and the like).

The reaction (b) serves to obtain the compound (Ib) by subjecting the appropriately protected tetrazole derivative (Ia) to deprotection.

In this reaction, the deprotection conditions vary with the protecting group (R) employed. When R is triphenyl methyl, 2-tetrahydropyranyl, methoxymethyl or ethoxymethyl, the reaction is conveniently conducted in an aqueous alcohol (e.g. methanol, ethanol, etc. ) containing about 0.5N to about 2N hydrochloric acid or acetic acid at room temperature for 1–10 hours.

The reaction (c) serves to obtain the halide (Id) by allowing a halogenating agent to react. This reaction is conducted, using about 1–5 moles of the halogenating agent, usually in a solvent. As the 10 halogenating agent, use is made of, for example, a chlorinating agent (e.g. chlorine, N-chlorosuccinimide, etc.), a brominating agent (e.g. bromine, N-bromosuccinimide, N-bromoacetamide, etc.), a fluorinating agent (e.g. fluorine, etc.), etc. As the solvent, use is made of halogenated hydrocarbons (e.g. chloroform, dichloromethane, dichloroethane, carbon tetrachloride, etc.), ethers (e.g. diethylether, dioxane, tetrahydrofuran(THF), etc.), acetic acid, trifluoroacetic acid, etc.

While the reaction conditions may vary depending on the combination of the halogenating agent and the solvent employed, it is preferable to conduct the reaction usually at 0° C. to room temperature for about 1–10 hours.

The reaction (d) serves to obtain carboxylic acid (If) by subjecting the ester (Ie) to hydrolysis. The hydrolysis is conducted, using about 1 to 3 moles of alkali relative to 1 mole of the compound (Ie), usually in a solvent such as an aqueous alcohol (e.g. methanol, ethanol, methyl cellosolve, etc.). As the alkali, use is made of, for example, sodium hydroxide, potassium hydroxide, etc.

The reaction is conducted at room temperature to 100° C. for 1–40 hours, preferably around the boiling point of the solvent for about 5–40 hours.

The reaction (e) serves to obtain the alkylthio compound (Ih) by subjecting the 2-mercapto compound (Ig) to alkylation in an organic solvent in the presence of a base.

The reaction is conducted, using 1 to about 3 moles of a base and 1 to about 3 moles of an alkylating agent realtive to 1 mole of the compound (Ig), usually in a solvent such as dimethylformamide, dimethylacetamide, dimethylsulfoxide, acetonitrile, acetone, ethylmethyl ketone, ethanol, methanol, water, etc.

As the base, use is made of caustic soda, potassium carbonate, sodium carbonate, sodium hydride, potassium t-butoxide, potassium hydroxide, etc.

As the alkylating agent, use is made of halogenides (e.g. methyl iodide, ethyl iodide, propyl iodide, butyl iodide or bromides or chlorides thereof).

While the reaction conditions may vary depending on the base, the alkylating agent and the solvent then employed, the reaction is conducted usually at 0° C. to the boiling point of the solvent for 1–5 hours.

The reaction (f) serves to obtain the compound (Ij) by leading the compound (Ih) to the sulfoxide (Ii) with a suitable oxidizing agent (e.g. m-chlorobenzoic acid, etc.), followed by the reaction with various nucleophilic reagents (e.g. alcohols, amines, mercaptans, etc.).

The reaction for obtaining the sulfoxide and sulfone compound (Ii) by oxidation of the compound (Ih) is conducted usually in a solvent such as halogenated hydrocarbons (e.g. dichloromethane, chloroform, dichloroethane, etc.) or ethers (e.g. tetrahydrofuran, dioxane, etc.). As the oxidizing agent, mention is made of an organic peracid e.g. m-chloroperbenzoic acid, etc., N-halocarboxylic amides e.g. N-bromosuccinic imide, etc., among others. Such oxidizing agents are preferably employed in a little excess amount to the equivalent relative to 1 mole of the compound (Ih). More specifically, use of 1 mole of the oxidizing agent gives a sulfoxide compound, while use of about 2 moles of the oxidizing agent affords a sulfone compound. The reaction is preferably conducted usually at 0° C. to room temperatures for 3–10 hours.

Further, the reaction (f) is to obtain the compound (Ij) by allowing the sulfoxide or sulfone compound (Ii) prepared as above to react with various nucleophilic reagents.

The reaction conditions may vary depending on the nucleophilic reagent employed. In the reaction with alcohols, alkoxides (e.g. sodium methoxide, sodium ethoxide, sodium propoxide, etc.) derived from the alcohol and sodium metal are preferably used. As the reaction solvent, alcohols used for nucleophilic reagents are used, and an alkoxide in about 2 to 5 times the amount relative to 1 mole of the compound (Ii) is allowed to react usually for about 1 to 3 hours at approximately the boiling point of the solvent.

In the reaction with amines, about 3 to 10 moles of an amine is used relative to 1 mole of the compound (Ii). As the solvent, alcohols (e.g. ethanol, etc.) are usually employed, but a large excess volume of amines can be used as well. The reaction is preferably conducted at the boiling point of the solvent to 150° C. for 1–10 hours.

The reaction (g) serves to obtain the compound (In) by protecting the tetrazole group in the presence of a base, then protecting the carboxyl group to give the ester compound (Im), followed by removing the protective group under acid conditions.

In the reaction to obtain the compound (Il) from the compound (Ik), an alkylating agent is used in an amount of about 1 to 1.5 mole relative to 1 mole of the compound (Ik). Examples of the solvents to be used for the reaction include halogenated hydrocarbons such as chloroform, methylene chloride, ethylene chloride, etc., ethers such as dioxane, tetrahydrofuran, etc., acetonitrile, pyridine, etc.

Examples of such bases include potassium carbonate, sodium carbonate, triethylamine, pyridine, etc.

Examples of such alkylating agents include halides such as triphenylmethyl chloride, methoxy methyl chloride, etc.

While reaction conditions vary with combinations of the base and the alkylating agent employed, it is preferable to conduct the reaction by using triphenylmethyl chloride at 0° C. to room temperature for 1–3 hours in methylene chloride in the presence of triethylamine.

In the reaction for producing the compound (Im) from the compound (I1) thus obtained, an alkylating agent is used in an amount of about 1 to 3 moles relative to 1 mole of the compound (Il).

Examples of the solvents to be used for the reaction include amides such as dimethylformamide, dimethylacetamide, etc., acetonitrile, dimethylsulfoxide, acetone, ethyl methyl ketone, etc.

Examples of the base include potassium carbonate, sodium carbonate, sodium hydroxide, potassium t-butoxide, etc.

Examples of the alkylating agent include halides such as cyclohexyl 1-iodoethyl carbonate, ethyl 1-iodoethyl carbonate, pivaloyloxymethyl iodide, etc. While reaction conditions vary with combinations of the base and the alkylating agent employed, it is preferable to subject the compound (II) to reaction in DMF, by adding the alkylating agent in the presence of potassium carbonate, at room temperatures for 30 minutes to one hour.

The reaction for deprotecting the compound (Im) thus obtained is conducted preferably in a manner similar to the reaction (b).

When a trityl group is used as the protecting group of the tetrazole group, it is preferable to conduct the reaction in methanol or ethanol, while adding 1N-HCl, at about room temperatures for about 30 minutes to one hour.

The reaction (h) serves to convert the nitrile compound (Io) into the tetrazole compound (Ib) by allowing the former to react with various azides in an organic solvent.

This reaction is conducted, using about 1 to 5 moles of an azide compound relative to 1 mole of the compound (Io), usually in a solvent such as dimethylformamide, dimethylacetamide, toluene, benzene, etc.

Examples of such azides include trialkyltin azide (e.g. trimethyltin azide, tributyltin azide, triphenyltin azide, etc.) and hydrazoic acid or its ammonium salt.

When an organotin azide compound is employed, the reaction is allowed to proceed, by using 1 to 4 times as many moles of the azide compound relative to the compound (Io), for about 1 to 4 days under reflux in toluene or benzene. And, when hydrazoic acid or its ammonium salt is subjected to the reaction, it is preferable to allow the reaction to proceed, by using about 1 to 5 times as many moles of sodium azide and ammonium chloride or tertiary amine (e.g. triethylamine, tributylamine, etc.) relative to the compound (Io), in dimethylformamide (DMF) at 100°–120° C. for 1–4 days. In this case, improvement may sometimes be observed in reaction time and yield by the addition of the azide compound in suitable fractions.

The reaction products obtained as above by the reactions (a) to (h) can be easily isolated by conventional isolation and purification methods, for example column chromatography, recrystallization and the like.

Incidentally, these compounds (I) can be led, by conventional methods, to salts with physiologically acceptable acids or bases. These salts include, for example, salts with an inorganic acid such as 10 hydrochloric acid, sulfuric acid, nitric acid or the like and, depending on the compounds, salts with an organic acid such as acetic acid, nitric acid, succinic acid, maleic acid or the like, salts with an alkali metal such as sodium, potassium or the like, and salts with an alkaline earth metal such as calcium or the like.

Among these compounds, the starting compound (II) can be synthesized by the methods described in, for example, the following literature references or methods analogous thereto.

(1) B. Heinz and R. Hellmuth, Monatsh, Chem., 107, 299(1976), (2) Y. Tominaga, H. Fujito, Y. Matsuda and G. Kobayashi, Heterocycles, i, 1871(1977), (3) T. Tominaga, H, Fujito, Y. Matsuda and G. Kobayashi, Heterocycles, 12, 401(1979), (4) B. R. Fishwick, D. K. Rowles and C. J. M. Stirling, J. Chem. Soc., Chem. Commun., 1983, 834, (5) Ph. Rossy, F. G. M. Vogel, W. Hoffmann, J. Paust and A. Neurrenbach, Tetrahedron Lett., 22, 3493(1981), (6) F. Outurquin and P. Claude, Bull. Soc. Chim. Fr., 1983, 153, (7) C. Galvez, F. Garcia and J. Garcia, J. Chem. Research, 1985., 296

And, among the starting compounds (III), the compound (III) wherein n denotes 1, i.e. the compound (IIIa), is commercially available, or can be readily obtained also by subjecting a compound (IV) to halogenomethylation according to the methods described in literature references, for example;

J. R. E. Hoover, A. W. Chow, R. J. Stedman, N. M. Hall, H. S. Greenberg, M. M. Dolan and R. J. Feriauto, J. Med. Chem., 7, 245 (1964), 2) R. J. Stedman, J. R. E. Hoover, A. W. Chow, M. M. Dolan, N. M. Hall and R. J. Feriauto, J. Med. Chem., 7, 251 (1964), 3) H. Gilman and R. D. Gorsich, J. Am. Chem. Soc., 78, 2217 (1956), 4) M. Orchin and E. Oscar Woolfolk, 67, 122 (1945)

Reaction (i)

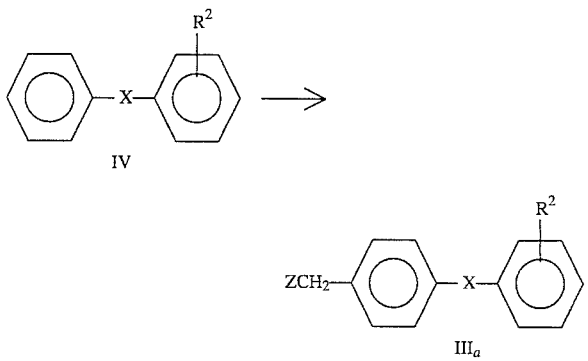

[wherein each symbol is of the same meaning as defined above]

Further, among the starting compounds (III), the compound (III) wherein n denotes 2, i.e. the compound (IIIb) can be obtained by subjecting the compound (IIIa) to the reaction in accordance with the reaction (j).

Reaction (j)

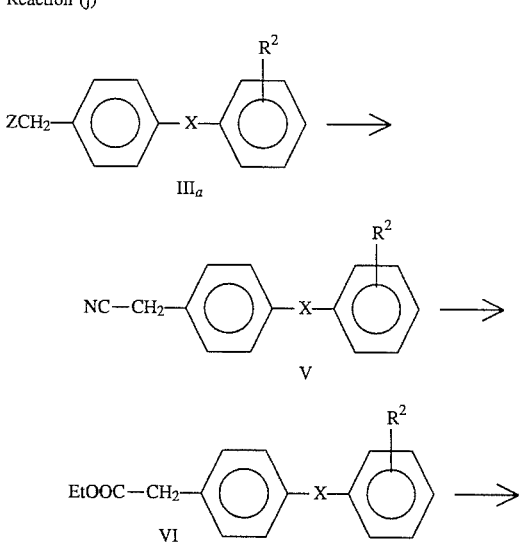

-continued

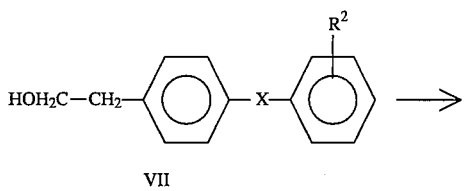

VII

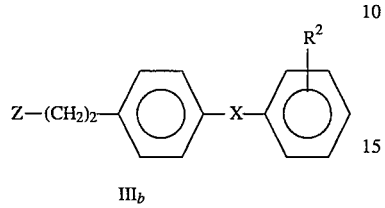

III$_b$

[wherein each symbol has the same meaning as above]

The compounds [I] and the salts thereof thus produced are of low toxicity, strongly inhibit the vasoconstrictive and hypertensive actions of angiotensin II, exert a hypotensive effect in animals, in particular mammals (e.g. human, dog, rabbit, rat, etc.), and therefore they are useful as therapeutics for not only hypertension but also circulatory diseases such as heart failure (hypertrophy of the heart, cardiac insufficiency, cardiac infarction or the like), cerebral apoplexy, nephritis with proteinuria, arteriosclerosis, etc.

For such therapeutic use as above, the compounds (I) and salts thereof can be orally or non-orally administered as pharmaceutical compositions or formulations, e.g. powders, granules, tablets, capsules, injections and the like, comprising at least one such compound alone or in admixture with pharmaceutically acceptable carriers, excipients or diluents.

The dose varies with the diseases to be treated, symptoms, subjects and administration routes, and it is preferable that a daily dose of 1 to 50 mg for oral administration or 1 to 30 mg for intravenous injection is divided into 2 to 3 administrations when used as an agent for the therapy of essential hypertension of adult human.

[Working Examples]

By the following formulation examples, reference examples, working examples and experimental examples, the present invention will be explained more concretely, but they should not be interpreted as limiting the invention in any manner.

Formulation Examples

When the compound (I) of the present invention is used as a therapeutic agent for circulatory disturbances such as hypertension, heart diseases, cerebral apoplexy, nephritis with proteinuria, arterioscelosis, etc., it can be used in accordance with, for example, the following formulations.

1. Capsules
(1) 2-ethylthio-4-methyl-1-[[2'-(1H-tetrazol-5-yl)- biphenyl-4-yl]methyl]thieno[3,4-d]imidazole-6- carboxylic acid     10 mg
(2) lactose     90 mg
(3) fine crystalline cellulose     70 mg
(4) magnesium stearate     10 mg one capsule     180 mg (1), (2), (3) and a half of (4) are mixed and granulated. To the granules is added the remainder of (4), and the whole is filled into gelatin capsules.

2. Tablets
(1) 2-ethylthio-4-methyl-1-[[2'-(1H-tetrazol-5-yl)-     10 mg biphenyl-4-yl]methyl]thieno[3,4-d]imidazole-6- carboxylic acid
(2) lactose     35 mg
(3) corn starch     150 mg
(4) fine crystalline cellulose     30 mg
(5) magnesium stearate     5 mg one tablet     230 mg (1), (2), (3), two thirds of (4) and a half of (5) are mixed and granulated. To the granules are added the remainders of (4) and (5), followed by subjecting the mixture to compression molding.

3. Injections
(1) 2-ethylthio-4-methyl-1-[[2'-(1H-tetrazol-5-yl)- biphenyl-4-yl]methyl]thieno[3,4-d]imidazole-6- carboxylic acid sodium salt     10 mg
(2) inositol     100 mg
(3) benzyl alcohol     20 mg one ampoule     130 mg (1), (2) and (3) are dissolved in distilled water for injection to make the whole volume 2 ml, which is filled into an ampoule. The whole process is conducted under sterile conditions.

4. Capsules
(1) 2-Methoxy-4-methyl-1-[[2'-(1H-tetrazol-5-yl)- biphenyl-4-yl]methyl]thieno[3,4-d]imidazole-6- carboxylic acid     10 mg
(2) lactose     90 mg
(3) fine crystalline cellulose     70 mg
(4) magnesium stearate     10 mg one capsule     180 mg (1), (2), (3) and a half of (4) are mixed and granulated. To the granules is added the remainder of (4), and the whole is filled into gelatin capsules.

5. Tablets
(1) 2-Methoxy-4-methyl-1-[[2'-(1H-tetrazol-5-yl)- biphenyl-4-yl]methyl]thieno[3,4-d]imidazole-6- carboxylic acid     10 mg
(2) lactose     35 mg
(3) corn starch     150 mg
(4) fine crystalline cellulose     30 mg
(5) magnesium stearate     5 mg one tablet     230 mg (1), (2), (3), two thirds of (4) and a half of (5) are mixed and granulated. To the granules are added the remainders of (4) and (5), followed by subjecting the mixture to compression molding.

6. Injections
(1) 2-Methoxy-4-methyl-1-[[2'-(1H-tetrazol-5-yl)- biphenyl-4-yl]methyl]thieno[3,4-d]imidazole-6- carboxylic acid sodium salt     10 mg
(2) inositol     100 mg
(3) benzyl alcohol     20 mg one ampoule     130 mg (1), (2) and (3) are dissolved in distilled water for injection to make the whole volume 2 ml, which is filled into an ampoule. The whole process is conducted under sterile conditions.

7. Capsules
(1) Acetoxymethyl 2-Methoxy-4-methyl-1-[[2'-(1H- tetrazol-5-yl)biphenyl-4-yl]methyl]thieno[3,4- d]imidazole-6-carboxylate     10 mg
(2) lactose     90 mg
(3) fine crystalline cellulose     70 mg
(4) magnesium stearate     10 mg one capsule     180 mg (1), (2), (3) and a half of (4) are mixed and granulated. To the granules is added the remainder of (4), and the whole is filled into gelatin capsules.

8. Tablets
(1) Acetoxymethyl 2-Methoxy-4-methyl-1-[[2'-(1H- tetrazol-5-yl)biphenyl-4-yl]methyl]thieno[3,4- d]imidazole-6-carboxylate     10 mg
(2) lactose     35 mg

| | |
|---|---|
| (3) corn starch | 150 mg |
| (4) fine crystalline cellulose | 30 mg |
| (5) magnesium stearate | 5 mg |
| one tablet | 230 mg |

(1), (2), (3) and two thirds of (4) and a half of (5) are mixed and granulated. To the granules is added the remainder of (4) and (5), followed by subjecting the mixture to compression molding.

REFERENCE EXAMPLE 1

2-Butylthieno[3,4-d]imidazole

A mixture of 3,4-diaminothiophene (1.7 g) and ethyl valeroimidate hydrochloride (3.0 g) in ethanol (30 ml) was stirred at room temperatures for 1.5 hour. The reaction mixture was concentrated and the residue was dissolved in a mixture of ethyl acetate and a saturated aqueous solution of sodium hydrogencarbonate. The organic layer was washed with water, dried and concentrated to dryness. The concentrate was purified by silica gel column chromatography to give crystals. Recrystallization from isopropyl ether afforded colorless crystals (0.72 g, 27%), m.p. 118°–120° C. $^1$H-NMR(200 MHz, CDCl$_3$)δ: 0.95(3H,t), 1.35–1.54(2H, m), 1.73–1.88(2H,m), 2.79(2H,t), 6.75(2H,br s), 8.50(1H,br s). IR(KBr)cm$^{-1}$:3200–2200, 1530, 1480, 1440, 1390, 1240, 1230, 1160, 830, 815, 760, 740.

REFERENCE EXAMPLE 2

Methyl 2,3-dihydro-4-methyl-2-oxothieno[3,4-d]imidazol-6-carboxylate

A mixture of methyl 3,4-diamino-2-methylthiophene-5-caryboxylate (1.9 g) and N,N'-dicarbonyl diimidazole (1.8 g) in DMF (10 ml) was stirred at 50° C. for one hour. To the reaction mixture was added water to give crystals. Recrystallization from methanol gave colorless needles (2.0 g, 95%), m.p. 341°–343° C.(dec.). $^1$H-NMR(200 MHz, DMSO-d$_6$)δ:2.33(3H,s), 3.74(3H,s), 10.71(1H,s), 11.06(1H, s). IR(KBr)cm$^{-1}$:3320, 3150, 1735, 1680, 1590, 1445, 1360, 1285, 1200, 1100, 975, 810, 755, 745.

| Elemental Analysis for C$_8$H$_8$N$_2$O$_3$S: | | | |
|---|---|---|---|
| | C(%) | H(%) | N(%) |
| Calcd.: | 45.28; | 3.80; | 13.20 |
| Found: | 45.44 | 3.72; | 13.23 |

REFERENCE EXAMPLE 3

Methyl 2,3-dihydro-4-methyl-2-thioxothieno[3,4-d]-imidazole-6-carboxylate

A mixture of methyl 3,4-diamino-2-methylthiophene-5-carboxylate (1.0 g) and N,N'-thiocarbonyldiimidazole (1.1 g) in DMF (5 ml) was stirred at 50° C. for one hour. To the reaction mixture was added water to give crystals. Recrystallization from DMF-water afforded colorless prisms (1.2 g, quantitatively), m.p. 285°–288° C. (dec.)
$^1$H-NMR(200 MHz,DMSO-d$_6$)δ: 2.41(3H,s), 3.76(3H,s), 12.5(1H,br s). IR(KBr)cm$^{-1}$:1700, 1570, 1485, 1440, 1425, 1415, 1330, 1200, 1180, 1100, 750.

REFERENCE EXAMPLE 4

Methyl 2-ethylthio-4-methylthieno[3,4-d]imidazole-6-carboxylate

A mixture of methyl 2,3-dihydro-4-methyl-2-thioxothieno[3,4-d]imidazole-6-carboxylate (1.1 g), ethyl iodide (0.75 g), 2N NaOH (2.4 ml) and methanol (30 ml) was stirred at room temperature for 3 hours. The reaction mixture was concentrated, and there was added water to give crystals. Recrystallization from ethyl acetate—hexane afforded colorless prisms (1.0 g, 83%), m.p. 159°–160° C. 1H-NMR(200 MHz,CDCl$_3$)δ: 1.44(3H,t), 2.62(3H,s), 3.30(2H,q), 3.87(3H,s), 9.55(1H,br s). IR(KBr)cm$^{-1}$:1690, 1675, 1665, 1650, 1620, 1545, 1465, 1440, 1330, 1320, 1240, 1120, 1105.

REFERENCE EXAMPLE 5

Methyl 4-methylthieno[3,4d]imidazole-6-carboxylate

A mixture of methyl 3,4-diamino-2-methylthiophene-5-carboxylate (1.9 g) in formic acid (5 ml) was heated under reflux for 4 hours. The reaction mixture was concentrated, and there was added water, then insolubles were filtered off. The filtrate was neutralized with an aqueous solution of sodium hydrogencarbonate to give crystals. Recrystallization from methanol afforded pale brown prisms (0.2 g, 38%), m.p. 266°–267° C(dec.).

| Elemental Analysis for C$_8$H$_8$N$_2$O$_2$S: | | | |
|---|---|---|---|
| | C(%) | H(%) | N(%) |
| Calcd.: | 48.97; | 4.11; | 14.28 |
| Calcd.: | 49.05; | 3.95; | 14.12 |

$^1$H-NMR(90 MHz, DMSO-d$_6$)δ: 2.60(3H,s), 3.79(3H,s), 8.20(1H,s) IR(KBr)cm$^{-1}$: 1690, 1525, 1505, 1465, 1440, 1370, 1315, 1300, 1265, 1200, 1160, 1100, 945, 875, 760.

In substantially the same manner as Reference Example 4, the following compounds were synthesized.

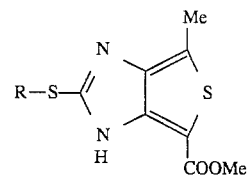

| Ref. Ex. | R | Yield (%) | m.p. (°C.) | $^1$H-NMR (200 MHz, CDCl$_3$)δ | IR (KBr)cm$^{-1}$ |
|---|---|---|---|---|---|
| 6 | Me | 56 | 178–179 | 2.62(3H, s), 2.73(3H, s), 3.87(3H, s) | 3275, 1670, 1650, 1620, 1540, 1460, 1440, 1320, 1215, 1100 |

-continued

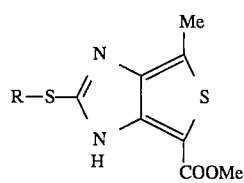

| Ref. Ex. | R | Yield (%) | m.p. (°C.) | ¹H-NMR (200 MHz, CDCl₃)δ | IR (KBr)cm⁻¹ |
|---|---|---|---|---|---|
| 7 | Pr | 89 | 110–111 | 1.06(3H, t), 1.72–1.90(2H, m), 2.62(3H, s), 3.28(2H, t), 3.87(3H, s), 9.20(1H, brs) | 3300, 1680, 1670, 1650, 1620, 1540, 1460, 1440, 1315, 1215, 1105 |
| 8 | iPr | 72 | 135–136 | 1.46(6H, d), 2.63(3H, s), 3.88(3H, s), 3.91–4.12(1H, m), 9.23(1H, brs) | 1690, 1620, 1540, 1460, 1360, 1210, 1100, 750 |
| 9 | All (Allyl) | 72 | 142–144 | 2.63(3H, s), 3.87(3H, s), 3.92(2H, td), 5.21(1H, qd), 5.37(1H, qd), 5.93–6.13(1H, m), 9.23(1H, brs) | 3200, 1660, 1650, 1620, 1540, 1460, 1440, 1320, 1220, 1100, 730 |
| 10 | Bu | 88 | 114–115 | 0.95(3H, t), 1.38–1.57(2H, m), 1.69–1.83(2H, m), 2.62(3H, s), 3.30(2H, t), 3.87(3H, s), 9.16(1H, brs) | 3275, 3225, 1670, 1650, 1460, 1440, 1315, 1300, 1220, 1100, 730 |
| 11 | Hex | 88 | 110–111 | 0.89(3H, t), 1.27–1.49(6H, m), 1.69–1.85(2H, m), 2.62(3H, s), 3.29(2H, t), 3.87(3H, s), 9.17(1H, brs) | 3275, 1665, 1610, 1540, 1460, 1450, 1435, 1300, 1210, 1100 |
| 12 | cyclo-Hex | 52 | 142–143 | 1.26–1.80(8H, m), 2.09–2.18(2H, m), 2.63(3H, s), 3.77–3.87(1H, m), 3.87(3H, s), 9.09(1H, brs) | 1710, 1700, 1620, 1460, 1430, 1370, 1310, 1210, 1190, 1100 |

REFERENCE EXAMPLE 13

2-Butyl-1-[[2'-(1H-tetrazol-5-yl)biphenyl-4-yl]methyl]-thieno[3,4-d]imidazole

To a solution of 2-butylthieno[3,4-d]imidazole (0.54 g) in DMF (3 ml) was added sodium hydride (60% oil, 0.13 g). The mixture was stirred for 15 minutes under ice-cooling, and there was added 4-[2-(N-trityltetrazole5-yl)phenyl]benzyl bromide, followed by stirring for 2 hours at room temperature. To the reaction mixture was added water and the mixture was extracted with ethyl acetate. The organic layer was washed with water, dried and concentrated to dryness. The concentrate was purified by silica gel column chromatography. The trityl compound thus obtained was dissolved in a mixture of methanol (18 ml) and chloroform (6 ml). To the solution was added 1N hydrochloric acid (7.5 ml), and the mixture was stirred for one hour at room temperature. The reaction mixture was concentrated to dryness and the residue was suspended with $H_2O$. The mixture was adjusted to pH 3–4 and extracted with chloroform. The organic layer was washed with water, dried and concentrated to dryness. The concentrate was purified by silica gel column chromatography to give crystals. Recrystallization from ethyl acetate—methanol afforded colorless crystals (0.53 g, 41%), m.p. 209°–211° C. ¹H-NMR(200 MHz, DMSO-d₆)δ: 0.88(3H,t), 1.27–1.46(2H,m), 1.59–1.74(2H, m), 5.22(2H,s), 6.66(1H,d), 7.05(1H,d), 7.08(2H,d), 7.18(2H,d), 7.50–7.71(4H,m). IR(KBr)cm⁻¹:1595, 1520, 1470, 1440, 1430, 1400, 815, 770, 760, 725.

| Elemental Analysis for $C_{23}H_{22}N_6S \cdot 0.2H_2O$: | | | |
|---|---|---|---|
| | C(%) | H(%) | N(%) |
| Calcd.: | 66.07; | 5.40; | 20.10 |
| Found: | 66.10; | 5.25; | 20.29 |

REFERENCE EXAMPLE 14

Methyl 2-ethylthiothieno[3,4-d]imidazole-6-carboxylate
14a) Methyl 3,4-diaminothiophene-2-carboxylate The title compound was obtained as colorless crystals according to the methods described in F. G. M. Vogel, J. Paust & A. Neurrenbach, Liebigs Ann. Chem., 1972(1980) and A. Fliri & K. Hohenlohe-Oehringen, Chem. Ber., 113, 607(1980). M.p. 95–97° C.
¹H-NMR(200 MHz,CDCl₃)δ: 3.83(3H,s), 6.40(1H,s).

14b) Methyl 2-mercaptothieno[3,4-d]imidazole-4-carboxylate

The title compound was obtained as pale yellow crystals from methyl 3,4-diaminothiophene-2-carboxylate obtained in Reference Example 14a) by the same procedures as for Reference Example 3, m.p. 250°–255° C. (decomp.).
¹H-NMR(200 MHz, DMSO-d₆)δ: 3.79(3H,s), 7.13(1H,s).

14c) Methyl 2-ethylthiothieno[3,4-d]imidazole-6carboxylate

The title compound was obtained as colorless prisms from methyl 2-mercaptothieno[3,4-d]imidazole-4-carboxylate obtained in Reference Example 14b) by the same procedure as for Reference Example 4, m.p. 164°–165° C.
¹H-NMR(200 MHz, CDCl₃)δ: 1.48(3H,t), 3.32(2H,q), 3.91(3H,s), 7.18(1H,s), 9.21(1H,br s).

WORKING EXAMPLE 1

Methyl 2-ethylthio-4-methyl-1-[[2'-(1H-tetrazol-5-yl)-biphenyl-4-yl]methyl]thieno[3,4-d]imidazole-6-carboxylate To a solution of methyl 2-ethylthio-4methylthieno[3,4-d]imidazole-6-carboxylate (0.77 g) in DMF (8 ml) was added sodium hydride (60% oil, 0.13 g) under ice-cooling, and the mixture was stirred for 15 minutes, and there was added 4-[2'-(N-trityltetrazol-5yl)phenyl] benzyl bromide (1.8 g), followed by stirring for 2 hours at room temperature. To the reaction mixture was added water and the mixture was extracted with ethyl acetate. The organic layer was washed with water, dried and then concentrated to dryness. The concentrate was purified by silica gel column chromatography to give the first fraction (1-substituted compound) and the second fraction (3-substituted compound). The yellow syrup (trityl compound) obtained from the first fraction was dissolved in a mixture of chloroform (10 ml) and methanol (35 ml). To the solution was added 1N-HCl (1.7 ml), and the mixture was stirred for one hour at room temperature. The reaction mixture was concentrated to dryness and to the mixture was added water. The mixture was adjusted to pH 3–4 with 1N NaOH, followed by extraction with chloroform. The extract was washed with water, dried and concentrated. The concentrate was purified by silica gel column chromatography. Crude crystals thus obtained were recrystallized from ethyl acetate—methanol to afford colorless needles (0.69 g, 46%), m.p. 216°–218° C. (dec.).

| Elemental Analysis for $C_{24}H_{22}N_6O_2S_2$: | | | |
|---|---|---|---|
| | C(%) | H(%) | N(%) |
| Calcd.: | 58.76; | 4.52; | 17.13 |
| Found: | 58.48; | 4.41; | 16.89 |

REFERENCE EXAMPLE 15

Methyl 2-ethylthio-4-methyl3-[[2'-(1H-tetrazol-5-yl)-biphenyl-4-yl]methyl] thieno[3,4-d]imidazole-6carboxylate The crystals obtained from the second fraction described in Working Example 1 were dissolved in chloroform (5 ml). To the solution was added 1N HCl (1.0 ml), and the mixture was stirred for one hour at room temperature. The reaction mixture was adjusted to pH 3–4 with 1N NaOH and concentrated to dryness. To the concentrate was added water and the mixture was extracted with chloroform. The extract was washed with water and dried ($Na_2SO_4$) and concentrated to dryness. The concentrate was purified by silica gel column chromatography to give crystals. Recrystallization from chloroform—isopropyl ether afforded pale yellow crystals (0.1 g, 7%), m.p. 192°–196° C. (dec.)

| Elemental Analysis for $C_{24}H_{22}N_6O_2S_2$: | | | |
|---|---|---|---|
| | C(%) | H(%) | N(%) |
| Calcd.: | 58.76; | 4.52; | 17.13 |

| Elemental Analysis for $C_{24}H_{22}N_6O_2S_2$: | | | |
|---|---|---|---|
| | C(%) | H(%) | N(%) |
| Found: | 59.16; | 4.65; | 17.31 |

$^1$H-NMR(200 MHz,CDCl$_3$)δ: 1.37(3H,t), 2.28(3H,s), 3.28(2H,q), 3.73(3H,s), 5.20(2H,s), 7.01–7.11(4H,m), 7.32–7.37(1H,m), 7.44–7.59(2H,m), 7.90–7.94(1H,m). IR(KBr)cm$^{-1}$: 1690, 1530, 1440, 1410, 1360, 1310, 1280, 1270, 1190, 1110, 760.

WORKING EXAMPLE 2

2-Ethylthio-4-methyl1-[[2'-(1H-tetrazol-5-yl)biphenyl-4-yl] thieno[3,4-d]imidazole-6-carboxylic acid Methyl 2-ethylthio-4-methyl-1-[[2'-(1H-tetrazol-5-yl)biphenyl-4-yl]methyl]thieno[3,4-d]imidazole-6carboxylate (0.25 g) was dissolved in a mixture of methanol (8 ml) and 1N NaOH (1.5 ml). The solution was heated for 12 hours under reflux. The reaction solution was adjusted to pH 3–4 with hydrochloric acid. Water was added to the reaction mixture, then precipitating crystals were recrystallized from methanol—ethyl acetate to afford colorless needles (0.16 g, 67%), m.p. 194°–195° C. (dec.).

| Elemental Analysis for $C_{23}H_{20}N_6O_2S_2$: | | | |
|---|---|---|---|
| | C(%) | H(%) | N(%) |
| Calcd.: | 57.97; | 4.23; | 17.63 |
| Found: | 57.68; | 4.36; | 17.49 |

$^1$H-NMR (200 MHz, DMSO-d$_6$)δ1.34(3H,t), 2.54(3H,s), 3.24(2H,q), 5.66(2H,s), 7.02–7.12(4H,m), 7.51–7.72(4H,m). IR(KBr)cm$^{-1}$: 1680, 1600, 1530, 1445, 1300, 1220, 1190, 1165, 1085, 775, 750

REFERENCE EXAMPLE 16

2-Ethylthio-4-methyl-3-[[2'-(1H-tetrazol-5-yl)biphenyl-4-yl]methyl]thieno[3,4-d]imidazole-6-carboxylic acid In substantially the same procedure as Working Example 2, the title compound was obtained as pale brown crystals (0.06 g) from methyl 2-ethylthio-4-methyl-3-[[2'-(1H-tetrazol-5-yl) biphenyl-4-yl]methyl]thieno[3,4-d]imidazole-6-carboxylate (0.1 g), m.p. 192°–195° C. (dec.).

| Elemental Analysis for $C_{23}H_{20}N_6O_2S_2 \cdot H_2O$: | | | |
|---|---|---|---|
| | C(%) | H(%) | N(%) |
| Calcd.: | 57.32; | 4.31; | 17.44 |
| Found: | 57.51; | 4.37; | 17.12 |

$^1$H-NMR(200 MHz,DMSO-d$_6$)δ: 1.39(3H,t), 2.28(3H,s), 3.35(2H,q), 5.28(2H,s), 7.08(4H,s), 7.53–7.74(4H,m). IR(KBr)cm$^{-1}$: 1610, 1600, 1530, 1435, 1410, 1400, 1360, 1350, 1280, 1110, 750

WORKING EXAMPLE 3

Methyl 4-methyl-1-[[2'-(1H-tetrazol-5-yl}biphenyl-4-yl]methyl]thieno[3,4-d]imidazole-6-carboxylate To a solution of methyl 4-methylthieno[3,4-d]-imidazole-6-carboxylate (0.20 g) in DMF (2 ml) was added sodium hydride (60% oil, 48 mg) under ice-cooling. The mixture was stirred for 15 minutes, and there which was added 4-[2'-(N-trityltetrazol-5-yl)phenyl] benzylbromide (0.68 g), followed by stirring for one hour at room temperature. To the reaction mixture was added water and the mixture was extracted with ethyl acetate. The extract was washed with water, dried and concentrated to dryness. The concentrate was purified by silica gel column chromatography to give the first fraction and the second fraction. The oily substance obtained from the first fraction was dissolved in chloroform (3 ml) - methanol (12 ml), to which was added 1N-HCl (0.5 ml), and the mixture was stirred for one hour at room temperature. The solvent was evaporated in vacuo. To the residue was added water, whose pH was adjusted to 3–4 with 1N NaOH, followed by extraction with chloroform. The extract was washed with water, dried and concentrated to dryness. The concentrate was purified by silica gel column chromatography. The crystals thus obtained were recrystallized from ethyl acetate -hexane to afford colorless needles (0.12 g, 28%), m.p. 188°–189° C.

Elemental Analysis for $C_{22}H_{18}N_6O_2S.0.2H_2O$:

|  | C (%) | H (%) | N (%) |
|---|---|---|---|
| Calcd.: | 60.87; | 4.27; | 19.36 |
| Found: | 60.83; | 4.17; | 19.24 |

$^1$H-NMR(200 MHz,DMSO-$d_6$)δ: 2.59(3H,s), 3.71(3H,s), 5.65(2H,s), 7.06(2H,d), 7.14(2H,d), 7.49–7.71(4H,m), 8.40(1H,s). IR(KBr)cm$^{-1}$:1680, 1600, 1530, 1425, 1330, 1275, 1225, 1140, 1080, 880, 750.

REFERENCE EXAMPLE 17

Methyl 6-methyl-1-[[2'-(1H-tetrazol-5-yl]biphenyl-4-yl]methyl]thieno [3,4-d]imidazole-4-carboxylate The crystals obtained from the second fraction described in Working Example 3 were dissolved in chloroform (3 ml) - methanol (12 ml). To the solution was added 1N HCl (0.5 ml), and the mixture was stirred for one hour at room temperature. The solvent was evaporated in vacuo and to the residue was added water. The mixture was adjusted to pH 3–4 with 1N NaOH, followed by extraction with chloroform. The extract was washed with water, dried and concentrated to dryness. The concentrate was purified by silica gel column chromatography. The crystals thus obtained were recrystallized from ethyl acetate—methanol to afford pale yellow prisms (50 mg, 12%), m.p. 225°–227° C. (dec.).

Elemental Analysis for $C_{22}H_{18}N_6O_2S_2.0.2H_2O$:

|  | C (%) | H (%) | N (%) |
|---|---|---|---|
| Calcd.: | 60.87; | 4.27; | 19.36 |
| Found: | 60.83; | 4.20; | 19/30 |

$^1$H-NMR(200 MHz,DMSO-$d_6$) :2.29(3H,s), 3.73(3H,s), 5.42(2H,s), 7.10(4H,s), 7.52–7.72(4H,m), 8.51(1H,s). IR(KBr)cm$^{-1}$:1690, 1500, 1445, 1435, 1330, 1285, 1200, 1110.

REFERENCE EXAMPLE 18

5-[4'-(4,6-Dibromo-2-butylthieno[3,4-d]imidazol-1-yl] -methylbipheny-2-yl]tetrazole K salt To a solution of 2-butyl-1-[[2' -( 1H-tetrazol-5-yl)biphenyl-4-yl]methyl]thieno [3,4-d]imidazole (0.15 g) in acetic acid (3 ml) was added dropwise a solution of bromine (0.11 g) in acetic acid (0.5 ml). The mixture was stirred for one hour at room temperature, then the solvent was evaporated in vacuo. To the residue was added water, which was extracted with ethyl acetate. The organic layer was washed with water and dried. The solvent was evaporated in vacuo, and the residue was purified by silica gel column chromatography. The syrup thus obtained was dissolved in methanol (1 ml), to which was added 2-ethyl hexanoic acid K salt (87 mg). To the mixture was added toluene (10 ml), which was concentrated under reduced pressure. Resulting precipitates were collected by filtration and dried to give fine crystals (47 mg, 21%), m.p. 246°–248° C. (dec.).

$^1$H-NMR(200 MHz,DMSO-$d_6$)δ: 0.85(3H,t), 1.28–1.42(2H, m), 1.55–1.70(2H,m), 5.30(2H,s), 6.98(2H,d), 7.13(2H,d), 7.24–7.37(3H,m), 7.52–7.57(1H,m). IR(KBr)cm$^{-1}$: 1490, 1475, 1405, 1355, 1110, 760.

Elemental Analysis for $C_{23}H_{19}Br_2KN_6S.0.5H_2O$:

|  | C (%) | H (%) | N (%) |
|---|---|---|---|
| Calcd.: | 44.60; | 3.25; | 13.57 |
| Found | 44.49; | 3.15; | 13.59 |

WORKING EXAMPLE 4

4-Methyl-1-[[2'-(1H-tetrazol-5-yl)biphenyl-4-yl]methyl]thieno[3,4-d]imidazole-6-carboxylic acid A solution of methyl 4-methyl-1-[[2'-(1H-tetrazol-5-yl)biphenyl-4-yl]methyl]thieno[3,4-d]imidazole-6-carboxylate (0.1 g) in a mixture of 1N NaOH (1.5 ml) and methanol (5 ml) was heated for two days under reflux. The reaction mixture was neutralized with 1N HCl to give crystals. Recrystallization from methanol—ethyl acetate afforded colorless crystals (0.1 g, quantitatively), m p 187°–189° C. (dec.).

Elemental Analysis for $C_{21}H_{16}N_6O_2S.¼MeOH.½H_2O$:

|  | C (%) | H (%) | N (%) |
|---|---|---|---|
| Calcd.: | 59.43; | 4.22; | 19.57 |
| Found: | 59.52; | 4.21; | 19.32 |

$^1$H-NMR(200 MHz,DMSO-$d_6$)δ: 2.57(3H,s), 5.66(2H,s), 7.05(2H,d), 7.18(2H,d), 7.48–7.70(4H,m), 8.36(1H,s). IR(KBr)cm$^{-1}$:1680, 1605, 1525, 1505, 1330, 1255, 1240, 1215, 1150, 775, 765.

WORKING EXAMPLE 5

Pivaloyloxymethyl 2-ethylthio-4-methyl-1-[[2'-(1H-tetrazol-5-yl) biphenyl-4-yl]methyl]thieno[3,4-d]-imidazole-6-carboxylate 5a) 2-Ethylthio-4-methyl-1-[[2'-(N-trityltetrazol-5-yl)biphenyl -4-yl]methyl]thieno[3,4-d]imidazole-6-carboxylic acid Trityl chloride (0.6 g) was added to a solution of 2-ethylthio-4-methyl-1-[[2'-(1H-tetrazol-5-yl)biphenyl-4-yl ]methyl]thieno[3,4-d]imidazole-6-carboxylic acid (0.92 g) and triethylamine (0.3 ml) in dichloromethane (20 ml). The mixture was stirred for 30 minutes at room temperature. The reaction mixture was washed with water, dried, and then the solvent was evaporated ...in vacuo. The residue was purified by silica gel column chromatography to give crystals. Recrystallization from ethyl acetate - hexane afforded colorless needles (1.36 g, 98%), m.p. 138°–140° C.

| Elemental Analysis for $C_{42}H_{34}N_6O_2S_2$: | | | |
|---|---|---|---|
| | C (%) | H (%) | N (%) |
| Calcd.: | 70.17; | 4.77; | 11.69 |
| Found: | 69.99; | 4.74; | 11.65 |

$^1$H-NMR(200 MHz,CDCl$_3$)δ: 1.34(3H,t), 2.62(3H,s), 3.22(2H,q), 5.51(2H,s), 6.88–7.04(10H,m), 7.16–7.32 (10H, m), 7.39–7.44(2H,m), 7.85–7.90(1H,m). IR(KBr)cm$^{-1}$: 1690, 1650, 1600, 1530, 1445, 1410, 1310, 1260, 1230, 1190, 1160, 755, 740, 690.

5b) Pivaloyloxymethyl 2-ethylthio-4-methyl-1-[[2'(1H-tetrazol-5-yl) biphenyl-4-yl]methyl]thieno[3,4-d]imidazole-6-carboxylate To a solution of the trityl compound (0.6 g) obtained in Working Example 5a) in DMF (5 ml) were added K$_2$CO$_3$ (0.15 g) and pivaloyloxymethyl iodide (0.25 g), and the mixture was stirred for one hour at room temperature. To the reaction mixture was added water, which was extracted with ethyl acetate. The extract was washed with water and dried, followed by evaporation of the solvent to give a syrupy substance. The syrup was dissolved in methanol (10 ml) - chloroform (5 ml). To the solution was added 1N HCl (6 ml), and the mixture was stirred for 30 minutes at room temperature. The reaction mixture was concentrated, and there was added water, followed by extraction with chloroform. The extract was washed with water and dried, followed by evaporating in vacuo the solvent. The residue was purified by silica gel column chromatography to afford colorless powdery crystals (0.33 g, 67%), m.p. 107°–110° C. (dec.).

| Elemental Analysis for $C_{29}H_{30}N_6O_2S_2$: | | | |
|---|---|---|---|
| | C (%) | H (%) | N (%) |
| Calcd.: | 58.96; | 5.12; | 14.23 |
| Found: | 58.84; | 5.37; | 13.93 |

$^1$H-NMR(200 MHz ,CDCl$_3$)δ: 1.14(9H,S), 1.42(3H,t), 2.63(3H,s), 3.30(2H, q), 5.67(2H,s), 7.14–7.25(4H,m) , 7.40–7.45(1H,m), 7.50–7.64(2H,m), 8.17–8.21(1H,m) IR(KBr)cm$^{-1}$: 2975, 1750, 1730, 1700, 1600, 1480, 1450, 1320, 1230, 1165, 1130, 1080, 1060, 1030, 985, 750, 730.

WORKING EXAMPLE 6

1-(cyclohexyloxycarbonyloxy)ethyl 2-ethylthio-4-methyl-1-[[2'-(tetrazol-5-yl) biphenyl-4-yl]methyl]thieno[3,4-d]imidazole-6-carboxylate To a solution of 2-ethylthio-4-methyl-1-[[2'-(N-trityltetrazol-5-yl)biphenyl-4-yl]methyl] thieno[3,4-d]imidazole-6-carboxylic acid (0.6 g) obtained in Working Example 5a) in DMF (5 ml) were added K2CO$_3$ (0.15 g), 1-(cyclohexyloxycarbonyloxy)ethyl chloride (0.21 g) and potassium iodide (85 mg). The mixture was stirred for one hour at 60° C. To the reaction mixture was added water, which was extracted with ethyl acetate. The extract was washed with water and dried, then the solvent was evaporated in vacuo to give a syrupy substance, which was dissolved in methanol (10 ml) and chloroform (5 ml). To the solution was added 1N HCl (6 ml), and the mixture was stirred for 30 minutes at room temperature. The reaction mixture was concentrated to dryness, and there was added water, followed by extraction with chloroform. The extract was washed with water and dried, then the solvent was evaporated in vacuo. The residue was purified by silica gel column chromatography to afford colorless powdery crystals (0.36 g, 66%), m.p. 105°–108° C. (dec.).

| Elemental Analysis for $C_{32}H_{34}N_6O_5S_2$: | | | |
|---|---|---|---|
| | C (%) | H (%) | N (%) |
| Calcd.: | 59.42; | 5.30; | 12.99 |
| Found | 59.66; | 5.56; | 12.58 |

$^1$H-NMR(200 MHz,CDCl$_3$)δ: 1.17–1.85(16H,m), 2.64(3H, s), 3.31(2H,q), 4.46–4.58(1H,m), 5.68(2H,d), 6.87 (1H,q), 7.14(4H,s), 7.41–7.46(1H,m), 7.48–7.63(2H,m), 8.08–8.13 (1H,m). IR(KBr)cm$^{-1}$: 2950, 1755, 1690, 1450, 1320, 1275, 1260, 1230, 1165, 1050, 1020, 1000, 935, 900, 750.

WORKING EXAMPLE 7

Methyl 4-methyl-2-methylthio-1-[[2'-(1H-tetrazol-5-yl)-biphenyl-4-yl]methyl]thieno [3,4-d]imidazole-6carboxylate By substantially the same procedure as Working Example 1, the title compound was obtained as pale yellow needles (0.85 g, 45%) from methyl 4-methyl-2-methylthiothieno[3, 4-d] imidazole-6-carboxylate (0.94 g), m.p. 221°–225° C.

| Elemental Analysis for $C_{23}H_{20}N_6O_2S_2 \cdot 0.4H_2O$: | | | |
|---|---|---|---|
| | C (%) | H (%) | N (%) |
| Calcd.: | 57.10; | 4.33; | 17.37 |
| Found: | 57.34; | 4.30; | 17.19 |

$^1$H-NMR(200 MHz, DMSO-d$_6$)δ: 2.56(3H,s 2.65(3H,s ), 3.69(3H,s), 5.63(2H,s), 7.06(4H,s) 7.50–7.70(4H,m). IR(KBr)cm$^{-1}$: 1700, 1600, 1460, 143 1425, 1320, 1235, 1185, 1170, 1090, 750.

WORKING EXAMPLE 8

Methyl 4-methyl-2-propylthio-1-[[2'-(1H-tetrazol-5-yl)-biphenyl-4-yl]methyl]thieno[3,4-d]imidazole-6carboxylate By substantially the same procedure as Working Example 1, the title compound was obtained as colorless plates (1.0 g, 53%) from methyl 4-methyl-2propylthiothieno [3,4-d] imidazole-6-carboxylate (1.0 g), m.p. 222°–226° C. (dec.).

| Elemental Analysis for $C_{25}H_{24}N_6O_2S_2 \cdot 0.5H_2O$: | | | |
|---|---|---|---|
| | C (%) | H (%) | N (%) |
| Calcd.: | 58.46; | 4.91; | 16.36 |
| Found | 58.39; | 4.87; | 16.31 |

$^1$H-NMR(200 MHz,DMSO-$d_6$)δ: 0.95(3H,t), 1.63–1.80(2H, m), 2.55(3H,s), 3.24(2H,t), 3.68(3H,s), 5.63 (2H,s), 7.05(4H,s), 7.51–7.71(4H,m). IR(KBr)cm$^{-1}$: 1700, 1600, 1455, 1430, 1320, 1240, 1165, 1085, 750.

REFERENCE EXAMPLE 19

Methyl 4-methyl-2-propylthio-3-[[2'-(1H-tetrazol-5-yl)-biphenyl-4-yl]methyl]thieno[3,4-d]imidazole-6carboxylate By substantially the same procedure as Reference Example 15, the title compound was obtained as colorless crystals (82 mg, 4%) from methyl 4-methyl-2-propylthiothieno [3,4-d]imidazole-6-carboxylate (1.0 g), m.p. 203°–208° C. (dec.).

| Elemental Analysis for $C_{25}H_{24}N_6O_2S_2 \cdot 0.5H_2O$: | | | |
|---|---|---|---|
| | C (%) | H (%) | N (%) |
| Calcd.: | 58.46; | 4.91; | 16.36 |
| Found: | 58.55; | 4.76; | 16.12 |

$^1$H-NMR(200 MHz,DMSO-$d_6$)δ: 1.00(3H,t), 1.68–1.86(2H, m), 2.29(3H,s), 3.36(2H,t), 3.78(3H,s), 5.31(2H,s), 7.03–7.12(4H,m), 7.51–7.73 (4H,m). IR(KBr)cm$^{-1}$:1690, 1530, 1440, 1430, 1410, 1360, 1340, 1320, 1270, 1190, 1105, 1070, 755.

WORKING EXAMPLE 9

Methyl 2-allylthio-4-methyl-1-[[2'-(1H-tetrazol-5-yl)-biphenyl-4-yl]methyl] thieno[3,4-d]imidazole-6-carboxylate By substantially the same procedure as Working Example 1, colorless needles (0.7 g, 44%) were obtained from methyl 2-allylthio-4-methylthieno[3,4-d]imidazole-6-carboxylate, m.p. 203°–205° C. (dec.).

| Elemental Analysis for $C_{25}H_{22}N_6O_2S_2$: | | | |
|---|---|---|---|
| | C (%) | H (%) | N (%) |
| Calcd.: | 59.74; | 4.41; | 16.72 |

-continued

| Elemental Analysis for $C_{25}H_{22}N_6O_2S_2$: | | | |
|---|---|---|---|
| | C (%) | H (%) | N (%) |
| Found: | 59.51; | 4.36; | 16.59 |

$^1$H-NMR(200 MHz,DMSO-$d_6$)δ: 2.56(3H, s), 3.67(3H,s), 3.95(2H,d), 5.12–5.18(1H,m), 5.28–5.37(1H,m), 5.63(2H, s), 5.87–6.08(1H,m), 7.06 (4H,s), 7.51–7.72(4H,m). IR(KBr)cm$^{-1}$: 1680, 1595, 1450, 1425, 1315, 1235, 1160, 1085, 750.

REFERENCE EXAMPLE 20

Methyl 2-allylthio-4-methyl-3-[[2'-(1H-tetrazol-5-yl)-biphenyl-4-yl]methyl] thieno[3,4-d]imidazole-6-carboxylate By substantially the same procedure as Reference Example 15, colorless needles (16 mg, 1.0%) were obtained from methyl 2-allylthio-4-methylthieno[3,4-d]imidazole-6-carboxylate (0.7 g), m.p. 132°–140° C. (dec.).

| Elemental Analysis for $C_{25}H_{22}N_6O_2S_2 \cdot 0.5H_2O$: | | | |
|---|---|---|---|
| | C (%) | H (%) | N (%) |
| Calcd.: | 58.69; | 4.53; | 16.43 |
| Found: | 58.73; | 4.36; | 16.27 |

$^1$H-NMR (200 MHz,DMSO-$d_6$)δ: 2.29(3H,s), 3.77 (3H,s), 4.06(2H,d), 5.16–5.22(1H,m), 5.30(2H,s), 5.34–5.44 (1H,m), 5.93–6.16(1H,m), 7.02–7.12(4H,m), 7.49–7.67(4H,m).

WORKING EXAMPLE 10

Methyl 2-isopropylthio-4-methyl-1-[[2'-(1H-tetrazol-5yl]biphenyl-4-yl]methyl]thieno[3,4-d]imidazole-6-carboxylate By substantially the same procedure as Working Example 1, colorless needles (0.62 g, 41%) were obtained from methyl 2-isopropylthio-4-methylthieno [3,4-d]imidazole-6-carboxylate (0.82 g), m.p. 210°–214° C. (dec.).

| Elemental Analysis for $C_{25}H_{24}N_6O_2S_2$: | | | |
|---|---|---|---|
| | C (%) | H (%) | N (%) |
| Calcd.: | 59.50; | 4.79; | 16.65 |
| Found: | 59.36; | 4.80; | 16.71 |

$^1$H-NMR(200 MHz,DMSO-$d_6$)δ: 1.40(6H,d), 2.56(3H,s), 3.68(3H,s), 3.89–4.03(1H,m), 5.61(2H,s), 7.03(4H,s), 7.49–7.70(4H,m). IR(KBr)cm$^{-1}$1680, 1590, 1445, 1425, 1325, 1315, 1240, 1160, 1150, 1085, 750.

REFERENCE EXAMPLE 21

Methyl 2-isopropylthio-4-methy1-3-[[2'(1H-tetrazol-5-yl)biphenyl-4-yl]methyl]thieno[3,4-d]imidazole-6-carboxylate By substantially the same procedure as Reference Example 15, colorless crystals (12 mg, 0.8%) were obtained from methyl 2-isopropylthio-4-methylthieno[3,4-d] imidazole-6carboxylate (0.82 g), m.p. 132°–138° C. (dec.).

$^1$H-NMR(200 MHz,DMSO-d$_6$)δ: 1.46(6H,d), 2.29(3H,s), 3.77(3H,s), 4.01–4.19(1H,m), 5.28(2H,s), 7.00–7.11 (4H, m), 7.47–7.66(4H,m).

WORKING EXAMPLE 11

Methyl
2-butylthio-4-methyl-1-[[2'-(1H-tetrazol-5-yl)-
biphenyl-4-yl]
methyl]thieno[3,4-d]imidazole-6-carboxylate By substantially the same procedure as Working Example 1, pale yellow prisms (0.8 g, 40%) were obtained from methyl 2-butylthio-4-methylthieno[3,4-d]imidazole-6-carboxylate (1.10 g), m.p. 196°–198° C. (dec.).

| Elemental Analysis for C$_{28}$H$_{26}$N$_6$O$_2$S$_2$: | | | |
|---|---|---|---|
| | C (%) | H (%) | N (%) |
| Calcd.: | 60.86; | 5.05; | 16.20 |
| Found: | 59.86; | 5.04; | 15.96 |

$^1$H-NMR(200 MHz,DMSO-d$_6$)δ: 0.88(3H,t), 1.29–1.47 (2H,m), 1.60–1.75(2H,m), 2.55(3H,s), 3.26 (3H,t), 3.68(3H,s), 5.62(2H,s), 7.04(4H,s), 7.50–7.70 (4H,m) IR(KBr)cm$^{-1}$: 1690, 1600, 1450, 1430, 1420, 1315, 1230, 1160, 1085, 750.

REFERENCE EXAMPLE 22

Methyl 2-butylthio-4-methyl-3-[[2'-(
1H-tetrazol-5-yl)-biphenyl-4-yl ]
methyl]thieno[3,4-d]imidazole-6-carboxylate By substantially the same procedure as Reference Example 15, pale yellow prisms (12 mg, 0.6%)were obtained from methyl 2-butylthio-4-methylthieno [3,4-d] imidazole-6-carboxylate (1.10 g) , m.p. 108°–110° C. (dec.).

| Elemental Analysis for C$_{26}$H$_{26}$N$_6$O$_2$S$_2$.H$_2$O: | | | |
|---|---|---|---|
| | C (%) | H (%) | N (%) |
| Calcd.: | 58.19; | 5.26; | 15.66 |
| Found: | 58.48; | 4.93; | 15.21 |

$^1$H-NMR(200 MHz,DMSO-d$_6$)δ: 0.93(3H,t), 1.34-1.52(2H,m), 1.66–1.81(2H,m), 2.28( 3H,s), 3.38(3H,t), 3.76(3H,s), 5.29(2H,s), 7.01–7.11(4H,m), 7.49–7.67(4H,m).

WORKING EXAMPLE 12

Methyl
2-hexylthio-4-methyl-1-[[2'-(1H-tetrazol-5-yl)-
biphenyl-4-yl]methyl]thieno[3,4-d]imidazole-6-
carboxylate By substantially the same procedure as Working Example 1, colorless needles (0.75 g, 31%) were obtained from methyl 2-hexylthio-4-methylthieno [3,4d]imidazole-6-carboxylate (1.25 g), m.p. 135°–136° C. (dec.).

| Elemental Analysis for C$_{28}$H$_{30}$N$_6$O$_2$S$_2$: | | | |
|---|---|---|---|
| | C (%) | H (%) | N (%) |
| Calcd.: | 61.51; | 5.53; | 15.37 |
| Found: | 61.28; | 5.53; | 15.30 |

$^1$H-NMR(200 MHz,CDCl$_3$)δ: 0.88(3H,t), 1.26–1.45(6H,m), 1.67–1.82(2H,m), 2.58(3H,s), 3.27(3H,t), 3.77(3H,s), 5.73(2H,s), 7.14–7.24(4H,m), 7.28–7.42(1H,m), 7.49–7.63 (2H,m), 7.17–8.22(1H,m). IR(KBr)cm$^{-1}$: 1680, 1595, 1450, 1425, 1315, 1235, 1190, 1160, 1085, 750.

REFERENCE EXAMPLE 23

Methyl 2-hexylthio-4-methyl-3-[[2'-(
1H-tetrazol-5-yl]-biphenyl-4-yl ] methyl]thieno
[3,4-d]imidazole-6-carboxylate By substantially the same procedure as Reference Example 15, pale yellow crystals (18 mg, 0.7%) were obtained from methyl 2-hexylthio-4-methylthieno[3,4-d] imidazole-6-carboxylate (1.25 g), m.p. 152°–154° C. (dec.).

| Elemental Analysis for C$_{28}$H$_{30}$N$_6$O$_2$S$_2$.0.4H$_2$O: | | | |
|---|---|---|---|
| | C (%) | N (%) | N (%) |
| Calcd.: | 60.72; | 5.60; | 15.17 |
| Found: | 60.91; | 5.36; | 15.18 |

$^1$H-NMR(200 MHz,CDCl$_3$)δ: 0.89(3H,t), 3.31(3H,t), 3.74(3H,s), 5.22(2H,s), 7.03–7.13(4H,m), 7.32–7.37 (1H, m), 7.46–7.60(2H,m), 7.95–8.00(1H,m).

WORKING EXAMPLE 13

Methyl
2-cyclohexyl-4-methyl-1[[-2'-(1H-tetrazol-5-yl)-
biphenyl-4-yl]methyl]
thieno[3,4-d]imidazole-6-carboxylate By substantially the same procedure as Working Example 1, colorless needles (0.48 g, 42%), were obtained from methyl 2-cyclohexylthio-4-methylthieno[3,4-d]imidazole-6-carboxylate (0.65 g), m.p.169°–171° C. (dec.).

| Elemental Analysis for C$_{28}$H$_{28}$N$_6$O$_2$S$_2$.0.5H$_2$O: | | | |
|---|---|---|---|
| | C (%) | H (%) | N (%) |
| Calcd.: | 60.74; | 5.28; | 15.18 |
| Found: | 60.93; | 5.21; | 15.15 |

¹H-NMR(200 MHz,CDCl₃ )δ: 1.25–1.77(8H,m), 2.08–2.17 (2H,m), 2.61(3H,s), 3.77(3H,s), 3.83–3.95(1H,m), 5.74(2H, s), 7.14–7.24(4H,m), 7.38–7.43(1H,m), 7.49–7.63 (2H,m), 8.19–8.23(1H,m). IR(KBr)cm⁻¹: 1690, 1605, 1450, 1440, 1320, 1240, 1170, 1100, 760.

WORKING EXAMPLE 14

2-Allylthio-4-methyl-1[[-2'-(1H-tetrazol-5-yl)biphenyl-4-yl]methyl]
thieno[3,4-d]imidazole-6-carboxylic acid To a solution of methyl 2-allylthio-4-methyl-1-[[2'-(1H-tetrazol-5-yl) biphenyl-4-yl]methyl]thieno[3,4d] imidazole-6-carboxylate (0.59 g) in a mixture of tetrahydrofuran (10 ml) and water (5 ml) was added lithium hydroxide monohydrate (0.15 g), and the mixture was stirred for 20 hours at 50° C. The reaction mixture was concentrated to dryness and to the residue was added water. The solution was adjusted to pH 3–4 with 1N HCl to give crystals. Recrystallization from methanol—ethyl acetate afforded colorless crystals (0.35 g, 60%), m.p. 135°–136° C. (dec.).

| Elemental Analysis for C₂₄H₂₀N₆O₂S₂.0.6H₂O: | | |
|---|---|---|
| C (%) | H (%) | N (%) |
| Calcd.: 57.72; | 4.28; | 16.83 |
| Found: 57.74; | 4.26' | 16.98 |

¹H-NMR(200 MHz,DMSO-d₆)δ: 2.54(3H,s), 3.93(2H,d), 5.10–5.16(1H,m), 5.27–5.36(1H,m), 5.66 (2H,s), 5.85–6.06(1H,m), 7.06(4H,s), 7.50–7.70 (4H,m). IR(KBr)cm⁻¹: 1675, 159 5, 1525, 1440, 1300, 1220, 1180, 1160, 1080, 925, 770, 750

WORKING EXAMPLE 15

4-Methyl -2-methylthio-1-[[2'-(1H-tetrazol-5-yl)biphenyl-4-yl] thieno[3,4imidazole-6-carboxylic acid In substantially the same manner as Working Example 14, the title compound was obtained as colorless crystals (0.35 g, 51%) from methyl 4-methyl- 2-methylthio-1-[[2'-(1H-tetrazol-5-yl)biphenyl-4yl] methyl]thieno[3,4-d]imidazole-6-carboxylate (0.71 g), m.p. 188°–190° C. (dec.).

| Elemental Analysis for C₂₂H₁₈N₆O₂S₂.0.2H₂O: | | |
|---|---|---|
| C (%) | H (%) | N (%) |
| Calcd.: 56.69; | 3.98; | 18.03 |
| Found: 56.59; | 3.79; | 18.01 |

H-NMR(200 MHz,DMSO-d₆)δ: 2.54(3H, s), 2.64(3H,s), 5.66(2H,s), 7.03–7.13(4 H,m) , 7.51–7.71(4H,m). IR(KBr)cm⁻¹: 1650, 1640 , 1590, 1530, 1450, 1435, 1340, 1325, 1305, 1170, 750.

WORKING EXAMPLE 16

4-Methyl-2-propylthio-1-[[2'-(1H-tetrazol-5-yl)biphenyl-4-yl]methyl]
thieno[3,4-d]imidazole-6-carboxylic acid In substantially the same manner as Working Example 14, the title compound was obtained as colorless crystals (0.5 g, 62%) from methyl 4-methyl-2-propylthio-1-[[ 2'-(1H-tetrazol-5-yl)biphenyl-4-yl]methyl]thieno [3,4-d]imidazole-6-carboxylate (0.84 g), m.p. 161°–162° C. (dec.).

| Elemental Analysis for C₂₄H₂₂N₆O₂S₂.0.4H₂O: | | |
|---|---|---|
| C (%) | H (%) | N (%) |
| Calcd.: 57.91; | 4.62; | 16.88 |
| Found: 57.90; | 4.43; | 16.90 |

¹H-NMR(200 MHz,DMSO-d₆)δ: 0.95 (3H,t), 1.61–1.80(2H,m), 2.53(3H,s), 3.23(2H,t), 5.67(2H,s), 7.02–7.11(4H,brs), 7.49–7.71(4H,m). IR(KBr)cm⁻¹: 1680, 1600, 1530, 1445, 1305, 1225, 1190, 1185, 1165, 770, 750.

REFERENCE EXAMPLE 24

4-Methyl-2-propylthio-3-[[2'-(1H-tetrazol-5-yl)biphenyl-4-yl]methyl]thieno
[3,4-d]imidazole-6-carboxylic acid In substantially the same manner as Working Example 14, the title compound was obtained as colorless crystals (28 mg, 65%) from methyl 4-methyl-2-propylthio-3-[[ 2'-(1H-tetrazol-5-yl)biphenyl-4yl] methyl]thieno[3,4-d]imidazole-6-carboxylate (45 mg), m.p. 192°–197° C.
¹H-NMR(200 MHz,DMSO-d₆)δ: 0.99(3H,t), 1.67–1.85(2H, m), 2.28(3H,s), 3.35(2H,t), 5.29(2H,s), 7.08(4H,s), 7.52–7.73(4H,m).

WORKING EXAMPLE 17

2-Isopropylthio-4-methyl-1-[[2'-(1H-tetrazol-5-yl]-biphenyl-4-yl]methyl]
thieno[3,4-d]imidazole-6-carboxylic acid In substantially the same manner as Working Example 14, the title compound was obtained as colorless needles (0.3 7 g, 68%) from methyl 2-isopropyl-4-methyl-1-[[ 2'-(1H-tetrazol-5-yl)biphenyl-4-yl] methyl]thieno[3,4-d ]imidazole-6-carboxylate (0.55 g) , m.p. 182°–184 ° C. (dec .).

| Elemental Analysis for C₂₄H₂₂N₆O₂S₂.0.5H₂O: | | |
|---|---|---|
| C (%) | H (%) | N (%) |
| Calcd.: 57.70; | 4.64; | 16.82 |
| Found: 57.87; | 4.95; | 16.88 |

¹H-NMR(200 MHz,DMSO-d₆)δ: 1.39(6H,d), 2.55(3H,s), 3.88–4.03 (1H,m), 5.66(2H,s) , 7.06(4H,s), 7.51–7.72(4H, m). IR(KBr)cm⁻¹: 1650, 1640, 1590, 1530, 1450, 1430, 1380, 1240, 1160, 1150, 930, 770, 750.

WORKING EXAMPLE 18

2-Butylthio-4-methyl-1-[[2',(1H-tetrazol-5-yl)biphenyl-4-yl]methyl]thieno[3,4-d]imidazole-6-carboxylic acid In substantially the same manner as Working Example 14, the title compound was obtained as colorless needles (0.47 g, 74%) from methyl 2-butylthio-4-methyl-1-[[ 2'-(1H-tetrazol-5-yl)biphenyl-4yl] methyl]thieno[3,4-d]imidazole-6-carboxylic acid (0.65 g), m.p.161°–163° C. (dec.).

| Elemental Analysis for $C_{25}H_{24}N_6O_2S_2 \cdot 0.4H_2O$: | | | |
|---|---|---|---|
| | C (%) | H (%) | N (%) |
| Calcd.: | 58.67; | 4.88; | 16.42 |
| Found: | 58.64; | 4.60; | 16.58 |

$^1$H-NMR(200 MHz,DMSO-$d_6$)δ: 0.89(3H,t), 1.28–1.47(2H, m), 1.60–1.74(2H,m), 2.54(3 H,s), 3.25(3H,t), 5.66(2H,s), 7.07(4H,s), 7.50–7.70(4 H,m). IR(KBr)cm$^{-1}$: 1640, 1590, 1530, 1450, 1315, 1160, 770, 750

WORKING EXAMPLE 19

2-Hexylthio-4-methyl-1-[[2'-( 1H-tetrazol-5-yl )biphenyl-4-yl ]methyl ] thieno[ 3,4-d ]imidazole-6-carboxylic acid In substantially the same manner as Working Example 14, the title compound was obtained as colorless needles (0.47 g, 78 %) from methyl 2-hexylthio-4-methyl-1 -[[ 2 '-( 1H-tetrazol-5-yl)biphenyl-4yl] methyl]thieno[3,4 -d ]imidazole-6-carboxylate (0.6 g), m.p. 150°–152° C. (dec.).

| Elemental Analysis for $C_{27}H_{28}N_6O_2S_2 \cdot 0.7H_2O$: | | | |
|---|---|---|---|
| | C (%) | H (%) | N (%) |
| Calcd.: | 59.47; | 5.43; | 15.41 |
| Found: | 59.31; | 5.36; | 15.51 |

$^1$H-NMR(200 MHz,DMSO-$d_6$)δ: 0.89(3H,t), 1.21–1.39(6H, m), 1.60–1.77(2H,m), 2.53 (3H,s), 3.24(3H,t), 5.65(2H,s), 7.01–7.10(4H,m), 7.49–7.70(4H,m). IR(KBr)cm$^{-1}$: 1650, 1640, 1600, 1530, 1460, 1440, 1320, 1260, 1250, 1160, 775, 750.

WORKING EXAMPLE 20

2-Cyclohexyl -4-methyl -1-[[2'-(1H-tetrazol-5yl)biphenyl-4-yl ] methyl ]thieno[3,4-d]imidazole-6-carboxylic acid In substantially the same manner as Working Example 14, the title compound was obtained as colorless needles (0.25 g, 64%) from methyl 2-cyclohexylthio-4-methyl-1-[[ 2'-(1H-tetrazol-5-yl)-biphenyl-4-yl]methyl] thieno[3,4-d] imidazole-6-carboxylate (0.4 g), m.p.187°–190° C. (dec.).

| Elemental Analysis for $C_{27}H_{26}N_6O_2S_2 \cdot 0.5H_2O$: | | | |
|---|---|---|---|
| | C (%) | H (%) | N (%) |
| Calcd.: | 60.09; | 5.04; | 15.57 |

| Elemental Analysis for $C_{27}H_{26}N_6O_2S_2 \cdot 0.5H_2O$: | | | |
|---|---|---|---|
| | C (%) | H (%) | N (%) |
| Found: | 60.02; | 4.81; | 15.51 |

$^1$H-NMR(200 MHz,DMSO-$d_6$)δ: 1.32°1.73(8H,m), 2.00–2.10(2H,m), 2.54(3H,s), 3.77–3.90(1H,m), 5.66(2H, s), 7.05(4H,s), 7.50–7.71 ( 4H,m). IR(KBr)cm$^{-1}$: 1640, 1600, 1540, 1460, 1450, 1440, 1335, 1320, 1260, 1250, 1160, 940, 760.

WORKING EXAMPLE 21

Methyl 2-ethylthio-1-[[ 2'-( 1H-tetrazol-5-y1 )biphenyl-4-yl]methyl]thieno[3,4-d]imidazole-6-carboxylate In substantially the same manner as Working Example 1, the title compound was obtained as colorless needles (0.35 g, 36%) from methyl 2-ethylthiothieno[3,4-d]imidazole-6-carboxylate (0.5 g), m.p.204°–206° C. (dec.).

| Elemental Analysis for $C_{23}H_{20}N_6O_2S_2$: | | | |
|---|---|---|---|
| | C (%) | H (%) | N (%) |
| Calcd.: | 57.97; | 4.23; | 17.63 |
| Found: | 57.79; | 3.96; | 17.44 |

$^1$H-NMR(200 MHz,CDCl$_3$)δ: 1.41(3H,t), 3.21(2H,q), 3.79(3H,s), 5.74(2H,s), 6.93(1H,s), 7.10–7.20(4H,m), 7.38–7.42(1H,m), 7.53–7.64(2H,m), 8.15–8.20(1H,m). IR(KBr)cm$^{-1}$: 1700, 1585, 1450, 1430, 1420, 1320, 1250, 1230, 1165, 1100, 1045, 755, 745.

REFERENCE EXAMPLE 25

Methyl 2-ethylthio-1-[[2'-(1H-tetrazol-5-yl)biphenyl-4-yl]methyl]thieno[3,4-d]imidazole-4-carboxylate In substantially the same manner as Reference Example 15, the title compound was obtained as colorless needles (0.27 g, 27%) from methyl 2-ethylthiothieno[3,4-d] imidazole-4-carboxylate (0.5 g), m.p. 173°–175° C. (dec.).

| Elemental Analysis for $C_{22}H_{18}N_6O_2S_2 \cdot 0.1H_2O$: | | | |
|---|---|---|---|
| | C (%) | H (%) | N (%) |
| Calcd.: | 57.75; | 4.26; | 17.57 |
| Found | 57.91; | 4.07; | 17.22 |

$^1$H-NMR(200 MHz,CDCl$_3$)δ: 1.41(3H,t), 3.34(2H,q), 3.79(3H,s), 5.09(2H,s), 6.54(1H,s), 7.10(4H,q), 7.30–7.34 (1H,m), 7.47–7.58(2H,m), 7.96–8.00(1H,m). IR(KBr)cm$^{-1}$: 1700, 1520, 1440, 1430, 1415, 1400, 1360, 1350, 1310, 1190, 1160, 1100, 760.

WORKING EXAMPLE 22

2-Ethylthio-1-[[2'- ( 1H-tetrazol-5-yl) biphenyl-4-yl]methyl ]thieno[3,4-d]imidazole-6-carboxylic acid In substantially the same manner as Working Example 14, the title compound was obtained as colorless needles (0.17 g, 87%) from methyl 2-ethylthio- 1- [[2'-(1H-tetrazol-5-yl ] methyl]thieno[3,4d]imidazole-6-carboxylate (0.2 g), m.p. 199°–201° C.

| Elemental Analysis for $C_{22}H_{18}N_6O_2S_2 \cdot 0.2H_2O$: | | | |
|---|---|---|---|
| | C (%) | H (%) | N (%) |
| Calcd.: | 56.47; | 4.01; | 17.96 |
| Found: | 56.68; | 3.68; | 17.59 |

$^1$H-NMR(200 MHz,DMSO-$d_6$)δ: 1.34(3H,t), 3.24(2H,q), 5.67(2H, s), 7.02–7.12 (4H,m), 7.49–7.70(5H,m). IR(KBr)cm$^{-1}$: 1690, 1590, 1500, 1440, 1410, 1360, 1340, 1315, 1240, 1180, 750, 735.

REFERENCE EXAMPLE 26

2-Ethylthio-1-[[2'(1H-tetrazol-5-yl)biphenyl-4-yl]methyl]thieno [3,4-d]imidazole-4-carboxylic acid In substantially the same manner as Working Example 14, the title compound was obtained as colorless needles (0.1 g, 68%) from methyl 2-ethylthio-1-[[ 2'-(1H-tetrazol-5-yl]methyl]thieno[3,4-d]imidazole-4-carboxylate (0.15 g), m.p. 220°–222° C. (dec.).

| Elemental Analysis for $C_{22}H_{18}N_6O_2S_2 \cdot 0.5H_2O$: | | | |
|---|---|---|---|
| | C (%) | H (%) | N (%) |
| Calcd.: | 56,04; | 4.06; | 17.82 |
| Found: | 55.86; | 4.10; | 17.93 |

$^1$H-NMR(200 MHz,DMSO-$d_6$)δ: 1,39(3H,t), 3.35(2H,q), 5.18(2H,s), 7.09(2H,d), 7.14(1H,s), 7.23(2H,d), 7.51–7.73 (4H,m). IR(KBr)cm$^{-1}$: 1675, 1520, 1435, 1360, 1335, 1290, 1270, 1250, 1180, 1160, 770, 745.

WORKING EXAMPLE 23

Methyl 2-methoxy-4-methyl-1-[[2'-(1H-tetrazol-5-yl)-biphenyl-4-yl] methyl]thieno[3,4-d]imidazole-6-carboxylate

23a) methyl 1-[(2'-cyanobiphenyl-4-yl)methyl]-2-ethylthio-4-methylthieno [3,4-d]imidazole-6-carboxylate To a solution of methyl 2-ethylthio-4-methylthieno[3,4-d] imidazole-6-carboxylate (5.7 g) in DMF (30 ml) was added sodium hydride (60% oil, 0.98 g) under ice-cooling. After stirring the reaction mixture for 20 minutes, to the mixture was added dropwise a solution of (2'-cyanobiphenyl-4-yl)methyl bromide (7.25 g) in DMF (20 ml), followed by stirring for one hour at room temperature. To the reaction mixture was added water, which was extracted with ethyl acetate. The extract was washed with water and dried, then the solvent was evaporated in vacuo. The residue was purified by silica gel column chromatography to give crystals. Recrystallization from ethyl acetate - hexane afforded pale yellow prisms (7.6 g, 77%), m.p. 149°–151° C.
$^1$H-NMR(200 MHz,CDCl$_3$)δ: 1.42(3H,t), 2.63(3H,s), 3.31(2H,q), 3.78(3H,s), 5.76(2H,s), 7.29(2H,d), 7.38–7.51 (4H,m), 7.58–7.66(1H,m), 7.72–7.77(1H,m). IR(KBr)cm$^{-1}$: 2220, 1690, 1600, 1450, 1430, 1315, 1300, 1230, 1160, 1085, 770, 750.

23b) Methyl 1-(2'-cyanobiphenyl-4-yl)methyl]-2-ethylsulfinyl-4-methylthieno [3,4-d]imidazole-6-carboxylate To a solution of the ethylthio compound (7.2 g) obtained in Working Example 23a) in dichloromethane (100 ml) was added m-chloroperbenzoic acid (3.3 g) under ice-cooling and the mixture was stirred for one hour. The reaction mixture was washed with a saturated aqueous solution of hydrogencarbonate and water. The solution was dried and concentrated to dryness. The residue was purified by silica gel column chromatography to give crystals. Recrystallization from ethyl acetate - hexane afforded pale yellow crystals (7.0g, 94%), m.p.150°–151° C.
$^1$H-NMR(200 MHz,CDCl$_3$)δ: 1.26(3H,t), 2.72(3H,s), 2.99–3.30 (2H,m), 3.82(3H,s), 5.97(1H,d), 6.43(1H,d), 7.32(2H,d), 7.39–7.52(4H,m), 7.59–7.68(1H,m), 7.73–7.76(1H,m). IR(KBr)cm$^{-1}$: 2220, 1700, 1590, 1530, 1450, 1435, 1315, 1230, 1160, 1090, 1070, 770, 750.

23c) Methyl 2-methoxy-4-methyl-1-[(2'-cyanobiphenyl-4-yl) methyl]thieno[3,4-d]imidazole-6-carboxylate To a suspension of the ethyl sulfinyl compound (1.0 g) obtained in Working Example 23b) in methanol (20 ml) was added 28% sodium methoxide (methanol solution, 0.62 g). The mixture was heated for 30 minutes under reflux. The reaction mixture was concentrated to dryness to give crystals. Recrystallization from ethyl acetate - methanol afforded pale yellow prisms (0.79 g, 88%), m.p.181°–182° C.

| Elemental Analysis for $C_{23}H_{19}N_3O_3S$: | | | |
|---|---|---|---|
| | C (%) | H (%) | N (%) |
| Calcd.: | 66.17; | 4.59; | 10.07 |
| Found: | 66.29; | 4.60; | 9.79 |

$^1$H-NMR(200 MHz,CDCl$_3$)δ: 2.58(3H,s), 3.79(3H,s), 4.15(3H,s), 5.63(2H,s), 7.34(2H,d), 7.38–7.51(4H,m), 7.58–7.67(1H,m), 7.72–7.77(1H,m). IR(KBr)cm$^{-1}$: 2225, 1700, 1620, 1580, 1540, 1460, 1450, 1440, 1400, 1385, 1335, 1235, 1110, 1060, 770, 760.

23d) Methyl 2-methoxy-4-methyl-1-[[2'-(1H-tetrazol-5-yl) biphenyl -4yl]methyl]thieno[3,4-d]imidazole-6-carboxylate A mixture of the cyano compound (0.75 g) obtained in Working Example 23c) and trimethylsilyl azide (1.85 g) in toluene (20 ml) were heated under reflux for 24 hours. The reaction mixture was concentrated, and there was added water, followed by extraction with chloroform. The extract was washed with water and dried, then the solvent was evaporated in vacuo. The residue was purified by silica gel column chromatography to give crystals. Recrystallization from ethyl acetate - methanol afforded colorless needles (0.67 g, 80%), m.p.173°–175° C. (dec.).

| Elemental Analysis for $C_{23}H_{20}N_6O_3S_2 \cdot 0.3H_3O$: | | | |
|---|---|---|---|
| | C (%) | H (%) | N (%) |
| Calcd.: | 59.29; | 4.46; | 18.04 |
| Found: | 59.50; | 4.60; | 17.74 |

$^1$H-NMR(200 MHz,CDCl$_3$)δ: 2.36(3H,s), 3.74(3H,s), 3.97(3H,s), 5.57(2H,s ), 7.10–7.20(4H,m), 7.38–7.43 (1H,m ), 7.49–7.64 (2H,m), 8.09–8.13(1H,m). IR(KBr)cm$^{-1}$: 1700, 1615, 1575, 1540, 1470, 1460, 1440, 1410, 1390, 1380, 1340, 1320, 1230, 1100, 1070, 1000, 760.

WORKING EXAMPLE 24

Methyl 3-ethoxy-4-methyl-1-[[2'-(1H-tetrazol-5-yl)-biphenyl-4-yl] methyl]thieno[3,4-d]imidazole-6-carboxylate 24a) Ethyl 2-ethoxy-4-methyl,1-[(2'-cyanobiphenyl-4yl] methyl]thieno[3,4-d]imidazole-6-carboxylate A mixture of the ethyl sulfoxide (1.0 g) obtained in Working Example 23b) in ethanol (20 ml) containing sodium methoxide (0.167 g) was refluxed for 30 minutes. The reaction mixture was concentrated to dryness to give crystals and recrystallization from ethyl acetate - ethanol afforded pale yellow needles (0.86 g, 89%), m.p.153°–155° C.
$^1$H-NMR(200 MHz,CDCl$_3$)δ: 1.31(3H,t), 1.43(3H,t), 2.57(3H, s), 4.28(2H,q), 4.55(2H,q), 5.64(2H,s), 7.37(2H,d), 7.43–7.51(4H,m), 7.59–7.67(1H,m), 7.73–7.77(1H,m).

24b) Methyl 2-ethoxy-4-methyl-1-[[2'-cyanobiphenyl-4-yl)methyl] thieno[3,4-d]imidazole-6-carboxylate To a suspension ( 20 ml ) of the ethyl ester ( 0.86 g) obtained in Working Example 24a) in methanol (20 ml) was added 28% sodium methoxide (methanol solution, 0.75 and the mixture was refluxed for 3 hours. The reaction mixture was concentrated to dryness to give crystals and recrystallization from ethyl acetate - methanol afforded colorless needles (0.78 g, 94%), m.p. 155°–156° C.

| Elemental Analysis for $C_{24}H_{21}N_3O_3S$: | | | |
|---|---|---|---|
| | C (%) | H (%) | N (%) |
| Calcd.: | 66.80; | 4.91; | 9.74 |
| Found: | 66.69; | 4.78; | 9.67 |

$^1$H-NMR(200 MHz,CDCl$_3$)δ: 1.44(3H,t), 2.57(3H,s), 3.81(3H,s), 4.55(2H,q), 5.63(2H,s), 7.37(2H,d), 7.42–7.51 (4H,m), 7.59–7.67(1H,m), 7.73–7.77(1H,m). IR(KBr)cm$^{-1}$: 2225, 1690, 1620, 1570, 1535, 1450, 1330, 1215, 1060, 760.

24c) Methyl 2-ethoxy-4-methyl-1-[[2'-(1H-tetrazol-5-yl) biphenyl-4-yl]methyl]thieno[3,4-d]imidazole-6-carboxylate In substantially the same manner as Working Example 23d), the title compound was obtained as colorless needles (0.66 g, 79%) from the cyano compound (0.76 g) obtained in Working Example 24b), m.p.193°–195° C (dec.).

| Elemental Analysis for $C_{24}H_{22}N_6O_3S$: | | | |
|---|---|---|---|
| | C (%) | H (%) | N (%) |
| Calcd.: | 60.75; | 4.67; | 17.71 |
| Found: | 60.48; | 4.53; | 17.45 |

$^1$H-NMR(200 MHz,CDCl$_3$)δ: 1.41(3H,t) , 2.37(3H,s), 3.75(3H,s), 4.37(2H,d ), 5.57(2H,s ), 7.13(2H,d), 7.22(2H, d), 7.37–7.42 (1H,m), 7.49–7.63(2H,m), 8.10– 8.15(1H,m). IR(KBr)cm$^{-1}$:1685, 1610, 1570, 1530, 1440, 1430, 1380, 1330, 1230, 1060, 750.

WORKING EXAMPLE 25

Methyl 4-methyl-2-propoxy-1-[[2'-(1H-tetrazol-5-yl )-biphenyl-4-yl] methyl]thieno[3,4-d]imidazole-6-carboxylate 25a ) Methyl 4-methyl-2-propoxy-1-[[2'-cyanobiphenyl-4-yl) methyl]thieno[3,4-d]imidazole-6-carboxylate In substantially the same manner as Working Example 23c), the title compound was obtained as colorless needles (0.4 g, 41%) by heating the ethylsulfinyl compound (1.0 g) obtained in Working Example 23b) under reflux for 30 minutes in sodium propoxide (solution of sodium methoxide (0.2 g) in propanol (20 ml) ), m.p. 188°–190° C. (dec.).

| Elemental Analysis for $C_{25}H_{23}N_3O_3S \cdot 0.2H_2O$: | | | |
|---|---|---|---|
| | C(%) | H(%) | N(%) |
| Calcd.: | 66.86; | 5.25; | 9.36 |
| Found: | 66.78; | 5.09; | 9.25 |

$^1$H-NMR(200 MHz,CDCl$_3$)δ: 0.96(3H,t), 1.73–1.91(2H,m), 2.57(3H,s), 3.81(3H,s), 4.44(2H,t), 5.64(2H,s), 7.36(2H,d), 7.42–7.51(4H,m), 7.54–7.67(1H,m), 7.73–7.78(1H,m). IR(KBr)cm$^{-1}$: 2200, 1685, 1610, 1570, 1530, 1440, 1430, 1360, 1220, 1090, 750.

25b) Methyl 4-methyl -2-propoxy-1-[ [2'-(1H-tetrazol-5-yl) biphenyl-4-yl]methyl]thieno[ 3,4-d]imidazole-6-carboxylate In substantially the same manner as Working Example 23c), the title compound was obtained as colorless needles (0.35 g, 86%) by subjecting the cyano compound (0.37 g) obtained in Working Example 25a) to heating for 16 hours under reflux in a mixture of trimethyl tin azide (0.85 g) and toluene (15 ml), m.p. 206°–208° C. (dec.).

Elemental Analysis for $C_{25}H_{24}N_6O_3S$:

|  | C(%) | H(%) | N(%) |
|---|---|---|---|
| Calcd.: | 61.46; | 4.95; | 17.20 |
| Found: | 61.31; | 4.89; | 17.07 |

$^1$H-NMR(200 MHz, CDCl$_3$)δ: 0.95(3H,t), 1.70–1.88(2H, m), 2.38(3H,s), 3.76(3H,s), 4.27(2H,t), 5.57(2H,s), 7.13(2H, d), 7.23(2H,d), 7.37–7.41(1H,m), 7.49–7.64 (2H,m), 8.09–8.14(1H,m). IR(KBr)cm$^{-1}$: 1690, 1620, 1575, 1535, 1470, 1450, 1400, 1410, 1370, 1350, 1340, 1240, 1070, 970, 760.

WORKING EXAMPLE 26

Methyl 2-ethylamino-4-methyl-1-[[2'-(1H-tetrazol-5-yl)-biphenyl-4-yl]methyl]thieno[3,4-d]imidazole-6-carboxylate

26a) Methyl 2-ethylamino-4-methyl-1-[(2'-cyanobiphenyl-4yl]methyl]thieno[3,4-d]imidazole-6-carboxylate A mixture of the ethylsulfinyl compound (0.91 g) obtained in Working Example 23b) in a mixture of a 70% aqueous solution of ethylamine (10 ml) and ethanol (10 ml) was heated at 80° C. in an autoclave for 3 hours. The reaction mixture was concentrated to dryness. The concentrate was dissolved in ethyl acetate, washed with water and dried. The solvent was evaporated in vacuo, then the residue was purified by column chromatography on silica gel to give crystals. Recrystallization from ethyl acetate - hexane afforded colorless needles (0.45 g, 53%), m.p. 190°–191° C.
$^1$H-NMR(200 MHz,CDCl$_3$)δ: 1.18(3H,t), 2.56(3H,s), 3.38–3.52(2H,m), 3.76(3H,s), 3.96(1H,t), 5.73(2H,s), 7.32(2H,d), 7.40–7.56(4H,m), 7.60–7.69(1H,m), 7.74–7.79 (1H,m). IR(KBr)cm$^{-1}$: 3390, 2225, 1670, 1620, 1600, 1545, 1520, 1450, 1435, 1340, 1330, 1240, 760, 750.

26b) Methyl 2-ethylamino-4-methyl-1-[[2'-(1H-tetrazol-5-yl) biphenyl-4-yl]methyl]thieno[3,4-d]imidazole-6-carboxylate In substantially the same manner as Working Example 23d), the title compound was obtained as colorless needles (0.27 g, 52%) by heating the cyano compound (0.45 g) obtained in Working Example 25a) and trimethyltin azide (1.1 g) for 24 hours under reflux in toluene (20 ml), m.p.252°–255° C.

Elemental Analysis for $C_{24}H_{23}N_7O_2S \cdot 0.5H_2O$:

|  | C(%) | H(%) | N(%) |
|---|---|---|---|
| Calcd.: | 59.74; | 5.01; | 20.32 |
| Found: | 59.76; | 4.84; | 20.18 |

$^1$H-NMR(200 MHz,CDCl$_3$)δ: 1.14(3H,t), 2.40(3H,s), 3.32(2H,q), 3.64(3H,s), 5.58(2H,s), 7.03(4H,s), 7.49–7.70(4H,m). IR(KBr)cm$^{-1}$: 1705, 1680, 1670, 1630, 1480, 1440, 1340, 1335, 1270, 1220, 1095, 1075, 760.

WORKING EXAMPLE 27

Methyl 4-methyl-2-propylamino-1-[[2'-(1H-tetrazol-5-yl) biphenyl-4-yl]methyl]thieno[3,4-d]imidazole-6-carboxylate

27a) Methyl 4-methyl-2-propylamino-1-[(2'-cyano biphenyl-4-yl)methyl]thieno[3,4-d]imidazole-6-carboxylate A mixture of the ethyl sulfinyl compound (1.0 g) obtained in Working Example 23b) and propylamine (20 ml) was heated under reflux for 3 days. The reaction mixture was concentrated to dryness. The concentrate was dissolved in ethyl acetate, washed with water and dried, followed by evaporating in vacuo the solvent. The residue was purified by column chromatography on silica gel to give crystals. Recrystallization from ethyl acetate - hexane afforded pale yellow needles (0.72 g, 75%), m.p.148°–150° C.
$^1$H-NMR (200 MHZ,CDCl$_3$)δ: 8:0.82 (3H,t), 1.47–1.66(2H, m), 2.56(3H,s), 3.33–3.42(2H,m) , 3.78(3H,s), 3.97(1H,t), 5.75(2H,s), 7. 34(2H,d), 7.4 1–7.57(4H,m), 7.61–7.69 (1H, m), 7.75–7.80(1H,m) IR(KBr)cm$^{-1}$: 3375, 2200, 1680, 1660, 1615, 1590, 1540, 1520, 1440, 13 30, 1230, 1090, 1070, 750.

27b) Methyl 4-methyl-2-propylamino-1-[[2'-(1H-tetrazol-5-yl) biphenyl-4yl]methyl]thieno[3,4-d]-imidazole-6-carboxylate In substantially the same manner as Working Example 23d), the title compound was obtained as colorless needles (0.66 g, 77%) by refluxing a mixture of the cyano compound (0.7 g) obtained in Working Example 27a) and trimethyltin azide (1.62 g) in toluene (20 ml) for 24 hours. m.p. 204°–208° C. (dec.)

Elemental Analysis for $C_{25}H_{25}N_7O_2S \cdot 0.5CHCl_3$:

|  | C(%) | H(%) | N(%) |
|---|---|---|---|
| Calcd.: | 55.97; | 4.70; | 17.92 |
| Found: | 56.08; | 4.54; | 17.68 |

$^1$H-NMR(200 MHz,CDCl$_3$)δ: 0.82(3H,t), 1.46–1.64(2H,m), 2.40(3H,s), 3.25(2H, t), 3.66(3H,s), 5.61(2H,s), 7.04(4H,s), 7.49–7.7 0(4H,m). IR(KBr)cm$^{-1}$: 1705, 1670, 1660, 1630, 1550, 1480, 1460, 1440, 1350, 1340, 1250, 1215, 1080, 760.

WORKING EXAMPLE 28

2-Methoxy-4-methyl-1-[[2'-(1H-tetrazol-5-yl)biphenyl-4yl]
methyl]thieno[3,4d]imidazole-6-carboxylic
acid By substantially the same procedure as Working Example 14, the title compound was obtained as colorless needles (0.3 g, 61%) from the methyl ester (0.5 g) obtained in Working Example 23. m.p. 187°–189° C. (dec.)

| Elemental Analysis for $C_{22}H_{18}N_6O_3S \cdot 0.5H_2O$: | | | |
|---|---|---|---|
| | C(%) | H(%) | N(%) |
| Calcd.: | 58.01; | 4.20; | 18.45 |
| Found: | 57.79; | 4.29; | 18.35 |

$^1$H-NMR(200 MHz,DMSO-d$_6$)δ: 2.47(3H,s), 4.05( 3H,s ), 5.51(2H,s), 7.04(2H,d), 7.12(2H,d), 7.50–7.70(4H,m). IR(KBr)cm$^{-1}$: 1660, 1620, 1580, 1540, 1450, 1400, 1385, 1375, 1340, 1320, 1240, 990, 760, 750.

WORKING EXAMPLE 29

2-Ethoxy-4-methyl-1-[[2'-(1H-tetrazol-5-yl)biphenyl-4-yl]
methyl]thieno[3,4-d]imidazole-6-carboxylic
acid By substantially the same procedure as Working Example 14, the title compound was obtained as colorless needles (0.34 g, 75%) from the methyl ester (0.45 g) obtained in Working Example 24. m.p. 171°–172° C. (dec.)

| Elemental Analysis for $C_{23}H_{20}N_6O_3S \cdot H_2O$: | | | |
|---|---|---|---|
| | C(%) | H(%) | N(%) |
| Calcd.: | 57.73; | 4.63; | 17.56 |
| Found: | 57.88; | 4.67; | 17.20 |

$^1$H-NMR(200 MHz,DMSO-d$_6$)δ: 1.31(3H,t), 2.46(3H,s), 4.46(2H,q), 5.49(2H,s), 7.04(2H,d), 7.13(2H,d), 7.47–7.67(4H,m). IR(KBr)cm$^{-1}$: 1680, 1615, 1570, 1540, 1460, 1420, 1380, 1350, 1335, 1320, 1230, 750.

WORKING EXAMPLE 30

4-Methyl-2-propoxy-1-[[2'-(1H-tetrazol-5-yl)-biphenyl-4-yl]
methyl]thieno[3,4-d]imidazole-6-carboxylic acid In substantially the same manner as Working Example 14, the title compound was obtained as colorless needles (0.16 g, 67%) from the methyl ester (0.23 g) obtained in Working Example 25. m.p.173°–175° C. (dec.)

| Elemental Analysis for $C_{24}H_{22}N_6O_3S \cdot 0.7H_2O$: | | | |
|---|---|---|---|
| | C(%) | H(%) | N(%) |
| Calcd.: | 59.17; | 4.84; | 17.25 |
| Found: | 59.09; | 4.73; | 17.34 |

$^1$H-NMR(200 MHz,DMSO-d$_6$)δ: 0.86(3H,t), 1.61–1.79(2H, m), 2.46(3H,s), 4.36(2H,t), 5.51(2H,s), 7.04(2H,d), 7.14(2H,d), 7.48–7.70(4H,m). IR(KBr)cm$^{-1}$: 1680, 1615, 1570, 1565, 1535, 1450, 1370, 1335, 1230, 750.

WORKING EXAMPLE 31

2-Ethylamino-4-methyl-1-[[2'-(1H-tetrazol-5-yl)
biphenyl-4-yl]methyl]thieno[3,4-d]imidazole-6-
carboxylic acid In substantially the same manner as Working Example 14, the title compound was obtained as colorless needles (0.2 g, 91%) from the methyl ester (0.2 g) obtained in Working Example 26. m.p. 201°–205° C. (dec.),

| Elemental Analysis for $C_{23}H_{21}N_7O_2S \cdot 0.5CHCl_3$: | | | |
|---|---|---|---|
| | C(%) | H(%) | N(%) |
| Calcd.: | 54.36; | 4.17; | 18.88 |
| Found: | 54.34; | 4.14; | 18.67 |

$^1$H-NMR(200 MHz,DMSO-d$_6$)δ: 1.13(3H,s), 2.39(3H,s) 3.31(2H,q), 5.62(2H,s), 7.04(4H,s), 7.49–7.69(4H,m). IR(KBr)cm$^{-1}$: 1660, 1630, 1560, 1530, 1460, 1450, 1380, 1360, 1340, 1100, 965, 780, 760, 740.

WORKING EXAMPLE 32

4-Methyl-2,propylamino-1-[[2'-(1H-tetrazol-5-yl)
biphenyl-4-yl]methyl]thieno[3,4-d]imidazole-6-
carboxylic acid In substantially the same manner as Working Example 14, the title compound was obtained as colorless needles (0.2 g, 48%) from the methyl ester compound (0.46 g) obtained in Working Example 27. m.p. 206°–209° C. (dec.)

| Elemental Analysis for $C_{24}H_{23}N_7O_2S \cdot 1.5H_2O$: | | | |
|---|---|---|---|
| | C(%) | H(%) | N(%) |
| Calcd.: | 57.59; | 5.24; | 19.59 |
| Found: | 57.86; | 5.15; | 19.62 |

$^1$H-NMR(200 MHz,DMSO-d$_6$)δ: 0.81(3H,t), 1.44–1.62(2H, m), 2.38(3H,s), 3.23(2H,t), 5.63(2H,s), 7.04(4H,s), 7.48–7.70 (4H,m). IR(KBr)cm$^{-1}$: 1670, 1660, 1630, 1550, 1545, 1460, 1350, 1340, 760.

WORKING EXAMPLE 33

2-Ethoxy-1-[[2'-(1H-tetrazol-5-y! ]biphenyl-4-yl]
methyl]thieno[3,4-d]imidazole-6-carboxylic acid 33a) Methyl
1-[(2'-cyanobiphenyl-4,yl)methyl]-2-ethylthiothieno[
3,4-d]imidazole-6-carboxylate To a solution of methyl 2-ethylthiothieno[3,4-d]-imidazole-4-carboxylate (1.81 g) obtained in Reference Example 14c) in DMF (15 ml) was added sodium hydride (60% oil, 0.33 g) under ice-cooling. To the mixture was added dropwise a solution of (2'-cyanobiphenyl-4yl)methyl bromide (2.25 g) in DMF (10 ml) and the reaction mixture was stirred for 60 hours at room temperature. To the reaction mixture was added water and the mixture was extracted with ethyl acetate. The extract was washed with water and dried. The solvent was evaporated in vacuo and the residue was purified by column chromatography on silica gel to give crystals. Recrystallization from ethyl acetate - hexane afforded colorless needles, m.p. 140°–142° C.
$^1$H-NMR(200 MHz,CDCl$_3$)δ: 1.45(3H,t), 3.32(2H,q), 3.81(3H,s), 5.79(2H,s), 7.21(1H,s), 7.31(2H,d), 7.38–7.53(4H,m), 7.59–7.67(1H,m), 7.73–7.77(1H,m).

33b) Methyl 1-[(2'-cyanobiphenyl-4-yl)methyl]-2-ethylsulfinylthieno[3,4-d]imidazole-6-carboxylate In substantially the same manner as Working Example 23b), the title compound was obtained as colorless prisms (1.2 g, 72%) from the ethylthio compound (1.6 g) obtained in Working Example 33a). m.p. 118°–119° C.
$^1$H-NMR(200 MHz,CDCl$_3$)δ: 1.30(3H,t), 3.08–3.36(2H,m), 3.86(3H,s), 6.02(1H,d), 6.47(1H,d), 7.33(2H,d), 7.40–7.53(4H,m), 7.57(1H,s), 7.60–7.68(1H,m), 7.73–7.77(1H,m).

33c) Methyl 2-ethoxy-1-[(2'-cyanobiphenyl-4yl)methyl]thieno[3,4-d]imidazole-6-carboxylate A mixture of the compound obtained in Working Example 33b) (0.8 g) in sodium ethoxide ethanolate (prepared from 0.19 g of sodium methoxide and 10 ml of ethanol) was heated for 20 minutes under reflux. The reaction mixture was concentrated to dryness and the residue was dissolved in ethyl acetate - water. The organic layer was dried and the solvent was evaporated in vacuo. The residue was dissolved in methanol (10 ml), to which was added 28% sodium methanolate (0.75 g), followed by heating for 8 hours under reflux. The reaction mixture was concentrated to dryness and the residue was purified by column chromatography on silica gel to give crystals. Recrystallization from ethyl acetate - hexane afforded colorless needles (0.33 g, 41%), m.p. 130°–131° C.
$^1$H-NMR(200 MHz,CDCl$_3$)δ: 1.46(3H,t), 3.84(3H,s), 4.57(2H,q), 5.66(2H,s), 7.05(1H,s), 7.35–7.52(6H,m), 7.59–7,67(1H,m), 7.67–7.78(1H,m).

33d) Methyl 2-ethoxy-1-[[(2'-(1H-tetrazol-5-yl)-biphenyl-4-yl]methyl]thieno[3,4-d]imidazole-6-carboxylate A mixture of the compound obtained in Working Example 33c) (0.3 g) and trimethylsilyl azide (0.74 g) in toluene (10 ml) was heated for 24 hours under reflux. The reaction mixture was concentrated to dryness, and the residue was partitioned between chloroform and water. The organic layer was washed with water and dried, then the solvent was evaporated in vacuo. The residue was purified by column chromatography on silica gel to give crystals. Recrystallization from ethyl acetate - methanol afforded colorless needles (0.2 g, 60 %), m.p.186°–188° C. (dec.).

| Elemental Analysis for C$_{23}$H$_{20}$N$_6$O$_3$S.0.3H$_2$O: | | | |
|---|---|---|---|
| | C(%) | H(%) | N(%) |
| Calcd.: | 59.29; | 4.46; | 18.04 |
| Found: | 59.23; | 4.38; | 17.93 |

$^1$H-NMR(200 MHz, CDCl$_3$)δ: 1.33(3)H,t), 3.74(3H,s), 4.48(2H,q), 5.50(2H,s), 7.04(2H,d), 7.13(2H,d), 7.44(1H,s), 7.50–7.70(4H,m) IR(KBr)cm$^{-1}$:1705, 1615, 1575, 1570, 1510, 1455, 1420, 1390, 1345, 1245, 770.

33e) 2-Ethoxy-1-[[2'-(1H-tetrazol-5-yl)biphenyl-4-yl]methyl]thieno[3,4-d]imidazole-6-carboxylic acid In substantially the same manner as Working Example 14, the title compound (0.08 g, 55%) was obtained as colorless crystals from the compound obtained in Working Example 33d) (0.145 g). m.p. 159°–162° C. (dec.)

| Elemental Analysis for C$_{22}$H$_{18}$N$_6$O$_3$S.0.5H$_2$O: | | | |
|---|---|---|---|
| | C(%) | H(%) | N(%) |
| Calcd.: | 58.01; | 4.20; | 18.45 |
| Found: | 58.03; | 4.26; | 18.19 |

$^1$H-NMR(200 MHz, DMSO-d$_6$)δ: 1.32(3H,t), 4.47(2H,q), 5.53(2H,s), 7.05(2H,d), 7.15(2H,d), 7.35(1H,s), 7.49–7.69(4H,m). IR(KBr)cm$^{-1}$:1690, 1680, 1600, 1560, 1450, 1380, 1330, 1200, 750.

WORKING EXAMPLE 34

5-Methyl-2-propyl-6-(1H-tetrazol-5-yl]-1-[[2'(1H-tetrazol-5-yl)biphenyl-4-yl]methyl]thieno[2,3-d]imidazole

34a) Methyl 3-amino-4-cyano-5-methylthiophene-2-carboxylate

To a stirred mixture of sodium hydride (60% oil, 2.0 g) in THF (5 ml) was added dropwise a solution of malononitrile (3.3 g) in THF (10 ml) under ice-cooling. The mixture was stirred for 10 minutes, and there was then added dropwise a solution of ethyl dithioacetate (6.0 g) in THF (10 ml) at room temperature. After stirring for further 20 minutes, the reaction mixture was concentrated to dryness, and the residue was dissolved in THF (40 ml). To the solution was added dropwise a solution of methyl chloroacetate (5.4 g) in THF (10 ml) at room temperature. The mixture was stirred for 30 minutes, and there were then added a solution of sodium methoxide (28% methanol solution, 1 ml) in isopropanol (50 ml), followed by stirring for 3.5 hours at room temperature. To the reaction mixture was added water to give crystals. Recrystallization from ethyl acetate afforded colorless prisms (4.6 g, 47%), m.p. 209°–210° C.
$^1$H-NMR(200 MHz,CDCl$^3$)δ: 2.58(3H,s), 3.83(3H,s), 5.76(2H,br s).

34b) Methyl 3-butyrylamino-4-cyano-5-methylthiophene-2-carboxylate

A solution of the compound obtained in Working Example 34a) (2.0 g) and butyryl chloride (2.0 g) in dioxane (30 ml) were heated for 5 hours under reflux. The reaction mixture was concentrated to dryness to give crystals. Recrystallization from ethyl acetate - hexane afforded colorless needles (2.5 g, 93%), m.p. 124°–125° C.
$^1$H-NMR(200 MHz,CDCl$_3$)δ: 1.03(3H,t), 1.80(2H,m), 2.46(2H,t), 2.68(3H,s), 3.89(3H,s), 9.40(1H,br s).

34c) Methyl 3-[N-butyryl-N-(2'-cyanobiphenyl-4-yl)-methyl]amino-4-cyano-5-methylthiophene-2-carboxylate A mixture of the compound obtained in Working Example 34b) (2.6 g), 2-cyano-4'-bromomethylbiphenyl (3.0 g) and potassium carbonate (1.5 g) in acetonitrile (50 ml) was heated for 12 hours under reflux. The reaction mixture was concentrated to dryness, and the residue was dissolved in ethyl acetate - water. The organic layer was washed with water and dried. The solvent was evaporated in vacuo, and the residue was purified by column chromatography on silica gel to afford a colorless syrupy product (4.5 g, quantitative).
$^{H-NMR}$(200 MHz,CDCl$_3$)δ: 0.90(3H,t), 1.68(2H,m), 2.08(2H,t), 2.64(3H,s), 3.73(3H,s), 4.91(1H,d), 5.00(1H,d), 7.31(2H,d), 7.38–7.48(4H,m), 7.63(1H,dt), 7.74(1H,d).

34d) 3-[N-butyryl-N-(2'-cyanobiphenyl-4-yl)methyl]-amino-4-cyano-5-methylthiophene-2-carboxylic acid A mixture of the compound obtained in Working Example 34c) (4.5 g) in a mixture of methanol (45 ml) and 2N-NaOH (7.4 ml) was stirred for 1.5 hour at room temperature. The reaction mixture was concentrated in vacuo and the residue was dissolved in water. To the solution was added 1N HCl (15 ml), and the mixture was extracted with ethyl acetate. The organic layer was washed with water and dried, then the solvent was evaporated in vacuo to give a white powder (4.0 g, 93%).
$^{H-NMR}$(200 MHz,CDCl$_3$)δ: 0.89(3H,t), 1.59–1.77(2H,m), 1.98–2.21(2H,m), 2.66(3H,s), 4.76(1H,d), 5.16(1H,d), 7.29–7.49(6H,m), 7.63(1H,dt), 7.71(1H,d).

34e) tert-Butyl 3-[N-butyryl-N-(2'-cyanobiphenyl-4yl)methyl]amino-4-cyano-5-methylthiophene-2-carbamate A mixture of carboxylic acid obtained in Working Example 34d) (2.4 g), diphenylphosphoric acid azide (DPPA, 3.2 g) and triethylamine (1.2 g) in tert-butanol (25 ml) was stirred for 20 minutes at room temperature, followed by heating under reflux for 1.5 hour. The reaction mixture was concentrated to dryness, and the residue was dissolved in ethyl acetate. The solution was washed with water and dried, then the solvent was evaporated in vacuo. The residue was purified by column chromatography on silica gel to give crystals. Recrystallization from ethyl acetate - hexane afforded colorless prisms (2.2 g, 79%), m.p. 171°–172° C.
$^{H-NMR}$(200 MHz,CDCl$_3$)δ: 0.91(3H,t), 1.37(9H,s), 1.58–1.78 (2H,m), 1.96–2.16(2H,m), 2.56(3H,s), 4.41(1H,d), 5.32(1H,d), 6.29(1H,br s), 7.39–7.65(6H,m), 7.65(1H,dt), 7.77(1H,d).

34f) 2-Amino-3-[N-butyryl-N-(2'-cyanobiphenyl-4-yl)methyl]amino-4-cyano-5-methylthiophene A mixture of the carbamate obtained in Working Example 34e) (2.1 g) in 20% hydrogen chloride - methanol (40 ml) was heated for one hour under reflux. The reaction mixture was concentrated to dryness and to the residue was added a saturated aqueous solution of NaHCO$_3$, followed by extraction with ethyl acetate. The organic layer was washed with water and dried, then the solvent was evaporated in vacuo. The residue was crystallized form ethyl acetate - hexane to afford colorless needles (0.93 g, 66%), m.p.160°–161° C.
$^1$H-NMR(200 MHz,CDCl$_3$)δ: 0.91(3H,t), 1.61–1.72(2H,m), 2.06–2.15(2H,m), 2.51(3H,s), 3.20(2H,br s), 3.96(1H,d), 5.76(1H,d), 7.41–7.51(6H,m), 7.66(1H,dt), 7.47(1H,d).

34g) 6-Cyano-1-[(2'-cyanobiphenyl-4-yl]methyl]-5-methyl-2-propylthieno[2,3-d]imidazole A solution of the compound obtained in Working Example 34f) (1.9 g) in 10% hydrogen chloride - ethanol (55 ml) was heated for 5 days under reflux. The reaction mixture was concentrated to dryness and to the residue was added a saturated aqueous solution of NaHCO3, followed by extraction with ethyl acetate. The extract was washed with water and dried, then the solvent was evaporated in vacuo. The residue was purified by column chromatography on silica gel to afford pale yellow powder (1.6 g, 89%).
$^1$H-NMR(200 MHz,CDCl$_3$)δ: 1.02(3H,t), 1.85(2H,m), 2.70(3H,s), 2.79(2H,t), 5.47(2H,s), 7.21(2H,d), 7.41–7.57 (4H,m), 7.65(1H,dt), 7.76(1H,d).

34h) 5-Methyl-2-propyl-6-(1H-tetrazol-5-yl]-1-[[2'-(1H-tetrazol-5-yl]biphenyl-4-yl]methyl]thieno[2,3-d]imidazole A mixture of the compound obtained in Working Example 34g) (1.2 g) and trimethyltin azide (2.9 g) in toluene (30 ml) was heated for 3 days under reflux. The precipitated syrupy product was dissolved in a mixture of methanol (20 ml) and 1N HCl (12 ml). The solution was stirred for 30 minutes at room temperature. The reaction mixture was adjusted to pH 3–4 with 1N NaOH. The reaction mixture was extracted with chloroform. The extract was washed with water and dried, then the solvent was evaporated in vacuo. The residue was purified by column chromatography on silica gel to give crystals. Recrystallization from methanol - ethyl acetate afforded pale yellow needles (0.87 g, 62%), m.p. 237°–238° C. (dec.).

| Elemental Analysis for $C_{24}H_{22}N_{10}S \cdot MEOH$: | | |
| --- | --- | --- |
| C(%) | H(%) | N(%) |
| Calcd.: 58.35; | 5.09; | 27.22 |
| Found: 58.44; | 4.93; | 27.45 |

$^1$H-NMR(200 MHz,DMSO-d$_6$)δ: 0.92(3H,t), 1.67 (2H,m), 2.53(3H,s), 2.73(2H,t), 5.51(2H,s), 6.61(2H,d), 6.90(2H,d), 7.46(1H,d) 7.51–7.71 ( 3H,m ). IR(KBr)cm$^{-1}$:1570, 150 1465, 1445, 1020, 1000, 915, 780, 760.

WORKING EXAMPLE 35

4-Methyl-2-propyl-1-[[2'-(1H-tetrazol-5-yl)biphenyl-4yl]methyl]thieno[3,4-d]imidazole-6-carboxylic acid

35a) tert-Butyl-amino-4-ethoxycarbonyl-5-methylthiophene-2-carboxylate

In substantially the same manner as Working Example 34a), the title compound was obtained as colorless prisms (2.5 g, 17%) from ethyl cyanoacetate (5.7 g), m.p. 87°–88° C.
$^1$H-NMR(200 MHz,CDCl$_3$)δ: 1.39(3H,s), 1.55(9H,s), 2.62(3H,s), 4.34(2H,q).

35b) tert-Butyl 3-butyrylamino-4-ethoxycarbonyl-5-methylthiophene-2-carboxylate In substantially the same manner as Working Example 34b), the title compound was obtained as colorless syrup (2.8 g, quantitatively) from the compound (2.5 g) obtained in Working Example 35a).
$^1$H-NMR(200 MHz,CDCl$_3$)δ: 1.01(3H,t), 1.33(3H,t), 1.55(9H,s), 1.75(2H,m), 2.38(2H,t), 2.58(3H,s), 4.30(2H,q), 9.58(1H,br s).

35c) tert-Butyl 3-[[N-butyryl-N-(2'-cyanobiphenyl-4-yl) methyl]amino-4-ethoxycarbonyl-5-methylthiophene-2-carboxylate In substantially the same manner as Working Example 34c), the title compound was obtained as colorless syrup (3.8 g, 97%) from the compound (2.8 g) prepared in Working Example 35b).
$^1$H-NMR(200 MHz,CDCl$_3$)δ: 0.89(3H,t), 1.19(3H,t), 2.66(3H,s), 3.86–1.46 (9H,s), 1.65(2H,m), 2.08(2H,t), 7.31(2H,d), 7.38–4.41 (2H,m), 4.52(1H,d), 5.04(1H,d), 7.38–7.46 (4H,m), 7.62(1H,dt), 7.75(1Hd).

2-tert-Butoxycarbonyl-3-[[N-butyryl-N-(2'-cyanobiphenyl-4-yl) methyl]amino]-5-methylthiophene-4cyanobiphene-4-carboxylic acid The compound obtained in Working Example 35c) (1.9 g) was dissolved in a mixture of 1N NaOH (5.6 ml) and ethanol (20 ml), and the solution was stirred for 6 hours at 70° to 80° C. The reaction mixture was concentrated to dryness and the residue was acidified by the addition of 1N HCl to give crystals. Recrystallization from isopropyl ether - ethyl acetate afforded colorless needles (1.2 g, 67%), m.p. 157°–158° C. (dec.).
$^1$H-NMR(200 MHz,CDCl$_3$)δ: 0.87(3H,t), 1.51(9H,s), 1.55–1.75 (2H,m), 1.98–2.18(2H,m), 2.64(3H,s), 4.24(1H, d), 5.40(1H,d), 7.30–7.47(6H,m), 7.63(1H,d), 7.73(1H,d).

35e) tert-Butyl 4amino-3-[[N-butyryl-N-(2'-cyanobiphenyl-4-yl) methyl]amino]-5-methylthiophene-2-carboxylate By substantially the same procedure as Working Example 34e), the title compound was obtained as colorless syrup (1.0 g, quantitatively ) from the carboxylic acid (1.2 g) prepared in Working Example 35d).
$^1$H-NMR(200 MHz,CDCl$_3$ )δ: 0.88(3H,t), 1.54(9H,s), 1.63(2H,m), 1.99–2.06(2H,m), 2.17(3H,s), 4.02(1H,g), 5.75(1H,d), 7.34–7.50(6H,m), 7.65(1H,dt), 7.75(1H,d). IR(Neat)cm$^{-1}$: 3430, 3350, 2220, 1710, 1660.

35f) Ethyl 4-methyl-2propyl-1-[(2'-cyanobiphenyl-4-yl)methyl]thieno[3,4-d]imidazole-6-carboxylate The compound obtained in Working Example 35e) (1.0 g) was dissolved in 10% hydrogen chloride - ethanol (16 ml). The solution was heated for 63 hours under reflux. The reaction mixture was concentrated to dryness and to the residue was added an aqueous solution of sodium hydrogencarbonate, followed by extraction with ethyl acetate. The extract was washed with water and dried, then the solvent was evaporated in vacuo. The residue was purified by column chromatography on silica gel to afford a pale yellow syrupy product (0.14 g, 14%).
$^1$H-NMR(200 MHz ,CDCl$_3$)δ: 0.99(3H,t), 1.27(3H,t), 1.78(2H,m), 2.66(2H,t), 2.67(3H,s), 4.23(2H,q), 5.86(2H,s), 7.18(2H,d), 7.39–7.53(4H,m), 7.63(1H,dt), 7.75(1H,d). IR(Neat)cm$^{-1}$: 2210, 1685, 1545, 1480, 1440, 1405, 1360, 1325, 1230, 1195, 1090, 755, 730.

35g) Ethyl 4-methyl-2-propyl-1-[[2'-(1H-tetrazol-5-yl) biphenyl-4-yl]methyl]thieno[3,4-d]imidazole-6-carboxylate In substantially the same manner as Working Example 23d), the title compound was obtained as colorless prisms (0.09 g, 56%) from the compound (0.14 g) prepared in Working Example 35f). m.p. 214°–215° C.

| Elemental Analysis for C$_{26}$H$_{26}$N$_6$O$_2$S.0.2H$_2$O: | | | |
|---|---|---|---|
| | C(%) | H(%) | N(%) |
| Calcd.: | 63.71; | 5.43; | 17.14 |
| Found: | 64.07; | 5.50; | 16.75 |

$^1$H-NMR(200 MHz,CDCl$_3$)δ: 0.97 (3H,t), 1.29(3H,t), 1.76(2H,m), 2.56(3H,s), 2.59(2H,t), 4.23(2H,q), 5.78(2H,s), 7.08(2H,d), 7.18(2H,d), 7.37–7.43(1H,m), 7.55–7.61(2H, m), 8.13–8.18(1H,m). IR(KBr)cm$^{-1}$:1690, 1540, 1325, 1230, 1095, 750.

35h) 4-Methyl-2-propyl-1-[[2'-(1H-tetrazol-5-yl)-biphenyl-4-yl] methyl]thieno[3,4-d]imidazole-6-carboxylic acid By substantially the same procedure as Working Example 14, the title compound was obtained as colorless prisms (0.063 g, 76%) from the compound (0.09 g) prepared in Working Example 35g). m.p. 206°–207° C. (dec.)

| Elemental Analysis for C$_{24}$H$_{22}$N$_6$O$_2$S.0.2H$_2$O: | | | |
|---|---|---|---|
| | C (%) | H (%) | N (%) |
| Calcd.: | 62.38; | 4.88; | 18.18 |
| Found: | 62.42; | 4.73; | 17.94 |

$^1$H-NMR(200 MHz,DMSO-d$_6$)δ: 0.88(3H,t), 1.62(2H,m), 2.55(3H,s), 2.56(2H,t), 5.79 ( 2H,s ), 7.03(4H,m), 7.49–7.71(4H,m). IR(KBr)cm$^{-1}$:1690, 1600, 1540, 1470, 1360, 1230, 1200, 770.

WORKING EXAMPLE 36

Acetoxymethyl 2-methoxy-4-methyl-1-[[2'-(1H-tetrazol-5-yl) biphenyl-4-yl]methyl]thieno[3,4-d]imidazole-6-carboxylate acid In substantially the same manner as Working Example 5, the title compound was synthesized.

36a) 2-Methoxy-4-methyl-1-[[2'-(N-trityltetrazol-5-yl] biphenyl-4-yl]methyl]thieno[3,4-d]imidazole-6-carboxylic acid In substantially the same manner as Working Example 5a), the title compound was obtained as colorless crystals (0.65 g, 41%) from the tetrazole compound (1.0 g) prepared in Working Example 28. m.p. 178°–180° C.

¹H-NMR(200 MHz,DMSO-d₆)δ: 2.48(3H,s), 3.95(3H,s), 5.47(2H,s), 6.82–6.87(6H,m), 6.99–7.08(4H,m), 7.25–7.63(12H,m), (12H,m), 7.67–7.80(1H,m). IR(KBr)cm⁻¹ :1675, 1570, 1530, 1450, 1395, 1220, 750, 710, 690.

36b) Acetoxymethyl 2-methoxy-4-methyl-1-[[2'-(1H-tetrazol-5-yl) biphenyl-4-yl]methyl]thieno[3,4-d]-imidazole-6-carboxylate In substantially the same manner as Working Example 5b), the title compound was obtained as colorless crystals (0.156 g, 60%) from the compound (0.51 g) prepared in Working Example 36a) and chloromethyl acetate (0.2 g). m.p. 156°–158° C. (dec.)

| Elemental Analysis for $C_{25}H_{22}N_6O_2S$: | | | |
|---|---|---|---|
| | C (%) | H (%) | N (%) |
| Calcd.: | 57.91; | 4.28; | 16.21 |
| Found: | 57.83; | 4.28; | 16.14 |

¹H-NMR(200 MHz,CDCl₃)δ: 2.05(3H,s), 2.49(3H,m), 4.06(3H,m), 5.54(2H,s), 5.81(2H,s), 7.14–7.23(4H,m), 7.40–7.44(1H,m), 7.51–7.65(2H,m), 8.15–8.19(1H,m). IR(KBr)cm⁻¹:1750, 1700, 1610, 1570, 1455, 1450, 1400, 1380, 1365, 1330, 1240, 1200, 1000, 980.

WORKING EXAMPLE 37

2-Ethyl-5-methyl-1-[[2'-(1H-tetrazol-5-yl)biphenyl-4-yl] methyl]thieno[2,3-d]imidazole-6-carboxylic acid By substantially the same procedures as Working Examples 34 and 35, the title compound was synthesized.

37a) tert-Butyl 4-ethoxycarbonyl-5-methyl-3-propionylamino-thiophene-2-carboxylate In substantially the same manner as Working Example 34b), the title compound was obtained as a yellow syrupy product (3.29 g, 92%) from the compound (3.0 g) prepared in Working Example 35a) and propionyl chloride (1.1 ml). ¹H-NMR(200 MHz ,CDCl₃)δ: 1.24(3H,t), 1.32(3H,t), 1.55(9H,s), 2.43(2H,q), 2.58(3H,s), 4.29 (2H,q), 9.56(1H,br s). IR(Neat)cm⁻¹:3325, 1720, 1690, 1670, 1570, 1410, 1360, 1240, 1160, 1050.

37b) tert-Butyl 3-[[N-(2'-cyanobiphenyl -4-yl)methyl-N-propionyl] amino]-4-ethoxycarbonyl-5-methylthiophene-2-carboxylate In substantially the same manner as Working Example 34c), the title compound was obtained as a pale yellow syrupy product (4.3 g, 84%) from the compound produced in Working Example 37a).
¹H-NMR(200 MHz,CDCl₃)δ: 1.10(3H,t), 1.19(3H,t), 1.46(9H,s), 2.13(2H,q), 2.65(3H,s), 3.81–4.10(2H,m), 4.50(1H,d), 5.04(1H,d), 7.30(2H,d), 7.38–7.45(4H,m), 7.58–7.66(1H,m), 7.73–7.77(1H,m).

37c) 3[-N-2'-cyanobiphenyl-4-yl)methyl-N-propionyl] amino-4ethoxycarbonyl-5-methylthiphene-2-carboxylic acid In substantially the same manner as Working Example 34d), the title compound was obtained as colorless needles (3.27 g, 85%) from the compound (4.3 g) prepared in Working Example 37b). m.p. 120°–122° C.
¹H-NMR(200 MHz,CDCl₃)δ: 1.09(3H,t), 1.28(3H,t), 2.03–2.27 (2H,m), 2.72(3H,s), 4.06–4.25(2H,m), 4.44(1H,d), 5.13(1H,d), 7.27–7.47(6H,m), 7.58–7.66(1H,m), 7.71–7.74 (1H,m).

37d) Ethyl 2-amino-3-[[N-(2'-cyanobiphenyl-4-yl)methyl-N-propionyl] amino]-5-methylthiophene-4-carboxylate By substantially the same procedures as Working Examples 34e) and 34f), the title compound was obtained as a pale yellow syrup (1.56 g, 53%) from the compound (3.14 g) prepared in Working Example 37c).
¹H-NMR(200 MHz,CDCl₃)δ: 1.03(3H,t), 1.33(3H,t), 2.07–2.18 (2H,m), 2.58(3H,s), 3.83(1H,d), 4.25(2H,q), 5.67(1H,d), 7.41–7.50(6H,m), 7.61–7.69(1H,m), 7.72–7.76 (1H,m). IR(Neat)cm⁻¹ :3420, 3325, 2200, 1700, 1650, 1630, 1380, 1310, 1295, 1215, 1050, 760, 750.

37e) Ethyl [1-(2'-cyanobiphenyl -4-yl)methyl]-2-ethyl -5-methylthieno [2,3-d]imidazole-6-carboxylate In substantially the same manner as Working Example 34g), the title compound was obtained as colorless needles (0.3 g, 20 %) from the compound (1.56 g) produced in Working Example 37d). m.p. 136°–138° C.
¹H-NMR(200 MHz,CDCl₃)δ: 1.22(3H,t), 1.37(3H,t), 2.75(3H,s), 2.77(2H,q), 4.23(2H,q), 5.79(2H,s), 7.09(2H,d), 7.40–7.51(4H,m), 7.59–7.68(1H,m), 7.74–7.78 (1H,m). IR(KBr)cm⁻¹:2220, 1705, 1475, 1400, 1375, 1365, 1325, 1290, 1235.

37f) Ethyl 2-ethyl-5-methyl-1-[[2'-(1H-tetrazol-5yl) biphenyl-4-yl)methyl]thieno[2,3d]imidazole-6-carboxylate In substantially the same manner as Working Example 34h), the title compound was obtained as colorless needles (0.23 g, 71% ) from the compound produced in Working Example 37e). m.p. 114°–116° C.

| Elemental Analysis for $C_{25}H_{24}N_6O_2S_2.0.5C_4H_8O_2$: | | | |
|---|---|---|---|
| | C (%) | H (%) | N (%) |
| Calcd.: | 62.77; | 5.46; | 16.27 |
| Found: | 62.65; | 5.41; | 16.29 |

¹H-NMR(200 MHz,CDCl₃)δ: 1.14(3H,t), 1.18(3H,t), 2.51(2H,q), 2.62(3H,s), 4.14(2H,q), 5.61(2H,s), 6.72(2H,d), 6.97(2H,d), 7.35–7.41(1H,m), 7.56–7.65 (2H,m), 7.95–8.02(1H,m) . IR(KBr)cm⁻¹:1705, 1500, 1410, 1325, 1300, 1240, 1210, 1045, 755.

37g) 2-Ethyl-5-methyl-1-[[2'-(1H-tetrazol-5-yl)biphenyl-4-yl]methyl]thieno[2,3-d]imidazole-6-carboxylic acid In substantially the same manner as Working Example 14, the title compound was obtained as colorless crystals (0.09 g, 80%) from the compound (0.13 g) produced in Working Example 37f). m.p. 272°–274° C. (dec.)

| Elemental Analysis for $C_{23}H_{20}N_6O_2S_2 \cdot 0.3H_2O$: | | | |
|---|---|---|---|
| | C (%) | H (%) | N (%) |
| Calcd.: | 61.40; | 4.61; | 18.68 |
| Found: | 61.45; | 4.61; | 18.52 |

$^1$H-NMR(200 MHz,DMSO-$d_6$)δ: 1.17 (3H,t), 2.67(2H,q), 2.69(3H,s), 5.76(2H,s), 6.91(2H,d), 7.04(2H,d), 7.49–7.71 (4H,m). IR(KBr)cm$^{-1}$:1680, 1490, 1480, 1405, 1375, 1325, 1300, 1240, 1205, 1070, 750, 705.

WORKING EXAMPLE 38

Methyl 2-ethyl-5-methyl-1-[[2-(1H-tetrazol-5-yl)biphenyl-4-yl]methyl]thieno[2,3-d]imidazole-6-carboxylate A solution of the ethyl ester (0.057 g) obtained in Working Example 37f) in methanol (2 ml) containing sodium methoxide (50 mg) was heated under reflux. The reaction mixture was concentrated to dryness and then dissolved in water, followed by adjusting the pH to about 4 with 1N HCl to give crystals. Recrystallization from ethyl acetate - methanol afforded colorless crystals (0.037 g, 73%), m.p.242°–245° C. (dec.).

| Elemental Analysis for $C_{24}H_{22}N_6O_2S_2 \cdot 0.1H_2O$: | | | |
|---|---|---|---|
| | C (%) | H (%) | N (%) |
| Calcd.: | 62.62; | 4.86; | 18.26 |
| Found: | 62.53; | 4.94; | 17.95 |

$^1$H-NMR(200 MHz,DMSO-$d_6$)δ: 1.19(3H,t), 2.67(3H,s), 2.70(2H,q), 3.63(3H,s), 5.63(2H,s), 6.88(2H,d), 7.04(2H,d), 7.48–7.70(4H,m). IR(KBr)cm$^{-1}$:1710, 1500, 1450, 1440, 1410, 1300, 1230, 1060, 770.

WORKING EXAMPLE 39

Methyl 2-Ethylthio-4-phenyl-1-[[2'-(1H-tetrazol-5yl)biphenyl-4-yl]methyl]thieno[3,4-d]imidazole-6-carboxylate

39a) Methyl 3,4-Diamino-5-phenylthiophene-2-carboxylate

The title compound was prepared by the same procedure as in reported by K. Hartke et al., [K. Hartke and B. Seib, Pharmazie, 25, 517 (1970)]. m.p. 148°–150° C. (lit, 118° C.) $^1$H-NMR(200 MHz,DMSO-$d_6$)δ: 3.76(3H,s), 7.38-7.53(3H, m), 7.58–7.64(2H,m), 7.69(4H,br).

39b) Methyl 2-Mercapto-4-phenylthieno[3,4d]imidazole-6-carboxylate

A solution of methyl 3,4-diamino-5-phenylthiophene-2-carboxylate (1.5 g) and thiocarbonyldiimidazole (1.1 g) in DMF (5 ml) was stirred at 50° C. for 1 hr. To the reaction mixture was added water to give crystals, which were recrystallized from DMF-$H_2O$ to give pale yellow crystals (1.7 g, quant.). m.p. 294°–296° C. (d)

| Elemental Analysis for $C_{13}H_{10}N_6O_2S_2$: | | | |
|---|---|---|---|
| | C (%) | H (%) | N (%) |
| Calcd.: | 53.77; | 3.47; | 9.65 |
| Found: | 53.72; | 3.49; | 9.67 |

$^1$H-NMR(200 MHz ,DMSO-$d_6$ )δ: 3.82(3H,s), 7.34–7.51(3H,m), 7.72–7.77 (2H,m) IR(KBr )cm$^{-1}$: 1685, 1640, 1575, 1550, 1500, 1475, 1440, 1410, 1280, 1195, 1170, 1140, 1015, 955, 830, 750, 720, 680.

39c) Methyl 2-Ethylthio-4-phenylthieno[3,4-d]imidazole-6-carboxylate

A solution of methyl 2-mercapto-4-phenylthieno[3,4-d]imidazole-6-carboxylate (1.7 g), ethyl iodide and 2N NaOH (3 ml) in methanol (30 ml) was stirred at room temperature for 6.5 hr. The reaction solution was concentrated to dryness and the residue was triturated with $H_2O$ to give a crystalline product. Recrystallization from MeOH-EtoAc to give pale yellow needles (1.3 g, 68%). m.p. 214°–215° C.

| Elemental Analysis for $C_{15}H_{14}N_2O_2S_2$: | | | |
|---|---|---|---|
| | C (%) | H (%) | N (%) |
| Calcd.: | 56.58; | 4.43; | 8.80 |
| Found: | 56.55; | 4.63; | 8.84 |

$^1$H-NMR(200 MHz,DMSO-$d_6$)δ: 1.43(3H,t), 3.33(2H,q), 3.83(3H,s), 7 .31-7.39(1H,m), 7.44–7.52(2H,m), 8.05–8.09 (2H,m) IR(KBr)cm$^{-1}$:1640, 1610, 1485, 1455, 1435, 1320, 1280, 1255, 1195, 1125, 1020, 755

39d] Methyl 2-Ethylthio-4-phenyl-1-[[2'-(1H-tetrazol-5-yl]biphenyl-4-yl]methyl]thieno[3,4-d]imidazole-6-carboxylate The title compound was obtained by the same procedure as in Working Example 1 as colorless needles (1.4 g, 61%) from methyl 2ethylthio4-phenylthieno [3,4-d]imidazole-6-carboxylate (1.3 g). m.p. 214°–216° C. (d)

| Elemental Analysis for $C_{29}H_{24}N_6O_2S_2 \cdot 0.2H_2O$: | | | |
|---|---|---|---|
| | C (%) | H (%) | N (%) |
| Calcd.: | 62.62; | 4.42; | 15.11 |
| Found: | 62.54; | 4.22; | 15.03 |

$^1$H-NMR(200MHz,DMSO-$d_6$)δ: 1.41(3H,t), 3.35(2H,q), 3.73(3H,s), 5.67(2H,s), 7.05(2H,d), 7.11(2H,d), 7.34–7.71

(7H,m), 8.07–8.13(2H,m) IR(KBr)cm$^{-1}$:1680, 1595, 1485, 1440, 1430, 1320, 1300, 1280, 1255, 1235, 1180, 1170, 1110, 1045, 960, 915, 750

WORKING EXAMPLE 40

2-Ethylthio-4-phenyl-1-[[2'-(1H-tetrazol-5-yl]biphenyl-4-yl]methyl]thieno[3,4-d]imidazole-6-carboxylic acid The title compound was obtained as yellow needles (0.64 g, 73%) from methyl 2-ethylthio-4-phenyl-1-[[2'-(1H-tetrazol-5-yl) biphenyl-4-yl]methyl]thieno[3,4d]imidazole-6-carboxylate (0.9 g) by the same procedure for Working Example 2. m.p. 229°–230° C. (d)

| Elemental Analysis for $C_{28}H_{22}N_6O_2S_2.0.5H_2O$: | | | |
|---|---|---|---|
|  | C (%) | H (%) | N (%) |
| Calcd.: | 61.41; | 4.23; | 15.35 |
| Found: | 61.69; | 3.95; | 15.31 |

$^1$H-NMR(200 MHz,DMSO-d$_6$)δ: 1.40(3H,t), 3.34(2H,q), 5.71(2H,s), 7.06(2H,d), 7.13(2H,d), 7.32–7.71(7H,m), 8.08–8.12(2H,m) IR(KBr)cm$^{-1}$:1635, 1585, 1525, 1485, 1450, 1320, 1310, 1280, 1165, 770, 760

WORKING EXAMPLE 41

Methyl 2-Ethylthio-4-propyl-1-[[2'-(1H-tetrazol-5yl) biphenyl-4-yl]methyl]thieno[3,4-d]imidazole-6-carboxylate

41a) Methyl 3,4-diamino-5-propylthiophene-2-carboxyalte

The title compound was prepared by the procedure reported by K. Hartke et al., [K. Hartke and B. Seib, Pharmazie, 25, 517(1970)] m.p. 185°° C. (d)
$^1$H-NMR(90 MHz,DMSO-d$_6$)δ: 0.97(3H,t), 1.43–1.83(2H, m), 2.80(2H,t), 3.73(3H,s), 8.33(5H,brs) IR(Nujol)cm$^{-1}$:3400, 3310, 2730, 2540, 1695, 1630, 1495, 1320

41b) Methyl 2-Mercapto-4-propylthieno[3,4-d]imidazole-6-carboxyalte

The title compound was obtained as pale yellow prisms in 95% yield by the same procedure as in Working Example 39b). m.p. 255°–260° C. (d)
$^1$H-NMR(90 MHz,DMSO-d$_6$)δ: 0.90(3H,t), 1.43–1.83(2H, m), 2.73(2H,t), 3.20(1H,s), 4.77(3H,s), 12.50(1H,brs) IR(Nujol)cm$^{-1}$:3160, 3100, 1670, 1575, 1435, 1330, 1310, 1205, 1110

41c) Methyl 2-Ethylthio-4-propylthieno[3,4-d]imidazole-6-carboxyalte

The title compound was obtained as colorless needles in 93% yield by the same procedure as in Working Example 39c). m.p. 135°– 136° C.
1H-NMR(90 MHz,CDCl$_3$)δ: 1.00(3H,t), 1.43(3H,t), 1.60–1.93 (2H,m), 2.97(2H,t), 3.30(2H,q), 3.87(3H,s), 9.30(1H,brs) IR(Nujol)cm$^{-1}$:3220, 1665, 1615, 1440, 1315, 1210, 1105

41d) Methyl 2-Ethylthio-4-propyl-1-[[2'-(1H-tetrazol-5-yl) biphenyl-4-y]methyl]thieno[3,4-d]imidazole-6-carboxyalte The title compound was obtained as colorless needles in 50% yield by the same procedure as in Working Example 1. m.p. 162°–163° C.

| Elemental Analysis for $C_{26}H_{26}N_6O_2S_2.H_2O$: | | | |
|---|---|---|---|
|  | C (%) | H (%) | N (%) |
| Calcd.: | 58.19; | 5.26; | 15.66 |
| Found: | 58.47; | 5.20; | 15.65 |

$^1$H-NMR(90 MHz,CDCl$^3$)δ: 1.00(3H,t), 1.40(3H,t), 1.60–2.00 (2H,m), 2.93(2H,t), 3.27(2H,t), 3.73(3H,s), 5.70(2H,s), 7.07–7.67(7H,m), 8.07–8.23(1H,m) IR(Nujol)cm$^{-1}$: 3360, 2720, 1685, 1600, 1450, 1430, 1325, 1245, 1170

WORKING EXAMPLE 42

2-Ethylthio-4-propyl-1-[[2'-(1H-tetrazol-5-yl)biphenyl-4-yl]methyl]thieno[3,4-d]imidazole-6-carboxylic acid The title compound was obtained as colorless needles in 82% yield by the same procedure as in Working Example 2. m.p. 187°–188° C. (d)

| Elemental Analysis for $C_{25}H_{24}N_6O_2S_2$: | | | |
|---|---|---|---|
|  | C (%) | H (%) | N (%) |
| Calcd.: | 59.50; | 4.79; | 16.65 |
| Found: | 59.35; | 4.56; | 16.69 |

$^1$H-NMR(90 MHz,DMSO-d$_6$)δ: 1.00(3H,t), 1.40(3H,t), 1.63–2.03 (2H,m), 2.97(2H,t), 3.27(2H,q), 5.70(2H,s), 7.07(2H,d), 7.17(2H,d), 7.43–7.73(4H,m) IR(Nujol)cm$^{-1}$:2720, 1635, 1590, 1530, 1450, 1385, 1320, 1260, 1160, 755

WORKING EXAMPLE 43

Methyl 4-Methyl-2-pentafluoroethyl-1-[[2'-(1H-tetrazol-5-yl) biphenyl-4,yl]methyl]thieno[3,4-d]imidazole-6-carboxylate

43a) Methyl 4-Methyl-2-pentafluoroethylthieno[3,4-d]imidazole-6-carboxylate

A mixture of methyl 3,4-diamino-5-methylthiophene-2-carboxylate (1.0 g) in pentafluoropropionic acid (8.9 g) was stirred at 100° C. for 6 hr. The reaction solution was concentrated to dryness and the residue was suspensed in water. The mixture was made basic with aqueous solution of K$_2$CO$_3$, followed by extraction with ethyl acetate. The organic layer was washed with water, dried and concentrated to dryness. The residue was purified by silica gel column chromatography to give crystals. Recrystallization from isopropyl ether-hexane gave colorless plates (0.86 g, 51%).

m.p. 156°–157° C.

| Elemental Analysis for $C_{10}H_7F_5N_2O_2S$: | | | |
|---|---|---|---|
| | C (%) | H (%) | N (%) |
| Calcd.: | 38.22; | 2.25; | 8.91 |
| Found: | 38.23; | 2.45; | 8.87 |

IR(KBr)cm$^{-1}$:1695, 1620, 1560, 1440, 1375, 1330, 1300, 1280, 1220, 1150, 1110, 1030, 840, 755, 750, 735

43b) Methyl 4-Methyl-2-pentafluoroethyl-1-[[2'-(1H-tetrazol-5yl) biphenyl-4-yl]methyl]thieno[3,4d]imidazole-6-carboxylate The title compound was obtained as colorless needles in 26% yield by the same procedure as in Working Example 39d). m.p. 184°–186° C.

| Elemental Analysis for $C_{24}H_{17}F_5N_6O_2S$: | | | |
|---|---|---|---|
| | C (%) | H (%) | N (%) |
| Calcd.: | 52.56; | 3.12; | 15.32 |
| Found: | 52.42; | 2.89; | 15.06 |

$^1$H-NMR(200 MHz,CDCl3)δ: 2.75(3H,s), 6.00(2H,s), 7.10(2H,d), 7.20(2H,d), 7.39–7.44(1H,m), 7.51–7.63(2H, m), 8.21–8.26(1H,m) IR(KBr)cm$^{-1}$:1705, 1600, 1550, 1480, 1450, 1440, 1420, 1345, 1320, 1260, 1240, 1225, 1200, 1190, 1140, 1110, 1095, 1045, 960, 940, 755, 735

WORKING EXAMPLE 44

4-Methyl-2-pentafluoroethyl-1-[[2'-(1H-tetrazol-5yl) biphenyl-4-yl]methyl]thieno[3,4-d]imidazole-6-carboxylic acid The title compound was obtained as colorless crystals in 32% yield by the same procedure as in Working Example 2. m.p. 201°–202° C. (d)

| Elemental Analysis for $C_{23}H_{15}F_5N_6O_2S_2 \cdot 0.2H_2O$: | | | |
|---|---|---|---|
| | C (%) | H (%) | N (%) |
| Calcd.: | 51.34; | 2.88; | 15.62 |
| Found: | 51.29; | 2.92; | 15.48 |

$^1$H-NMR(200 MHz,DMSO-d$_6$)δ: 2.69(3H,s), 6.00(2H,s), 6.96(2H,d), 7.04(2H,d), 7.50–7.67(4H,m) IR(KBr)cm$^{-1}$:1645, 1540, 1260, 1210, 1140, 1110, 960, 940, 745

WORKING EXAMPLE 45

Methyl 2-Heptafluoropropyl-4-methyl-1-[[2'-(1H-tetrazol-5-yl) biphenyl-4-yl]methyl]thieno[3,4-d]imidazole-6-carboxylate

45a) Methyl 2-Heptafluoropropyl-4-methylthieno[3,4-d]imidazole-6-carboxylate The title compound was obtained as colorless prisms in 53% yield by the same procedure as in Working Example 43a). m.p. 147°–148° C.

| Elemental Analysis for $C_{11}H_7F_7N_2O_2S$: | | | |
|---|---|---|---|
| | C (%) | H (%) | N (%) |
| Calcd.: | 36.27; | 1.94; | 7.69 |
| Found: | 36.38; | 1.83; | 7.99 |

$^1$H-NMR(200 MHz,CDCl$_3$)δ: 2.76(3H.S), 3.92(3H,S), 9.80(1H,brs) IR(KBr)cm$^{-1}$:1700, 1620, 1560, 1440, 1375, 1350, 1330, 1280, 1220, 1200, 1180, 1150, 1105, 980, 910, 865, 760, 745, 730

45b) Methyl 2-Heptafluoropropyl-4-methyl-1-[[2'-(1H-tetrazol-5-yl] biphenyl-4-yl]methyl]thieno[3,4d]imidazole-6-carboxylate The title compound was obtained as colorless needles in 33% yield by the same procedure as in Working Example 39b). m.p. 144°–145° C.

| Elemental Analysis for $C_{25}H_{17}F_7N_6O_2S$: | | | |
|---|---|---|---|
| | C (%) | H (%) | N (%) |
| Calcd.: | 50.17; | 2.86; | 14.04 |
| Found: | 50.03; | 2.95; | 13.84 |

$^1$H-NMR(200 MHz,CDCl$_3$)δ: 2.76(3H,s), 3.81(3H,s), 5.99(2H,s), 7.09(2H,d), 7.20(2H,d), 7.39–7.44(1H,m), 7.51–7.63(2H,m), 8.23–8.27(1H,m) IR(KBr)cm$^{-1}$:1700, 1600, 1545, 1480, 1435, 1330, 1235, 1205, 1130, 1120, 1090, 905, 860, 755, 735

WORKING EXAMPLE 84

2-Heptafluoropropyl-4-methyl-1-[[2'-(1H-tetrazol-5yl)bipheny-4-yl] methyl]thieno[3,4-d]imidazole-6carboxylic acid The title compound was obtained as colorless needles in 54% yield by the same procedure as in Working Example 2. m.p. 204°–205° C. (d)

| Elemental Analysis for $C_{24}H_{15}F_7N_6O_2S$: | | | |
|---|---|---|---|
| | C (%) | H (%) | N (%) |
| Calcd.: | 49.32; | 2.59; | 14.38 |
| Found: | 49.01; | 2.88; | 14.28 |

¹H-NMR(200 MHz,DMSO-d₆)δ: 2.69(3H,s), 5.99(2H,s), 6.93(2H,d), 7.04(2H,d), 7.49–7.70(4H,m) IR(KBr)cm⁻¹:1645, 1540, 1335, 1220, 1120, 870, 850

WORKING EXAMPLE 47

Methyl 2-Ethylthio-4-methylthio-1-[[2'(1H-tetrazol-5yl)biphenyl-4-yl]methyl]thieno[3,4-d]imidazole-6-carboxylate

47a) Methyl 3,4-diamino-5-methylthiothiophene-2-carboxylate

The title compound was prepared by a procedure like that by K. Hartke et al., [K. Hartke and B. Seib, Pharmazie, 25, 517(1970)]. m.p. 95°–97° C.
¹H-NMR(90 MHz,CDCl₃)δ: 2.33(3H,s), 3.60(2H,brs), 3.80(3H,s), 5.27(2H,brs) IR(Nujol)cm⁻¹: 3450, 3400, 3350, 1670, 1620, 1495, 1450, 1425, 1320, 1250, 1130

47b) Methyl 2-Mercapto-4-methylthiothieno[3,4-d]imidazole-6-carboxylate

The title compound was obtained as yellow prisms in 77% yield by the same procedure as in Working Example 39b). m.p. 240°–242° C. (d)
¹H-NMR(90 MHz,DMSO-d₆)δ: 2.53(3H,s), 3.27(1H,brs), 3.77(3H,s), 12.77(1H,brs) IR(Nujol)cm⁻¹:3200, 3125, 3075, 3020, 1680, 1625, 1555, 1490, 1430, 1330, 1290, 1190, 1165, 1070

47c) Methyl 2-Ethylthio-4-methylthiothieno[3,4-d]imidazole-6carboxylate

The title compound was obtained as colorless needles in 93% yield by the same procedure as in Working Example 39c). m.p. 170°–172° C.
H-NMR(90 MHz,CDCl₃)δ: 1.43(3H,t), 2.67(3H,s), 3.33(2H,q), 3.87(3H,s), 9.23(1H,brs) IR(Nujol)cm⁻¹:3200, 1655, 1615, 1510, 1440, 1315, 1150

47d) Methyl 2-Ethylthio-4-methylthio-1-[[2'-(1H-tetrazol-5-yl)biphenyl-4-yl]methyl]thieno[3,4d]imidazole-6-carboxylate The title compound was obtained as colorless needles in 79% yield by the same procedure as in Working Example 1. m.p. 200°– 201° C.

| Elemental Analysis for C₂₄H₂₂N₆O₂S₃: | | | |
|---|---|---|---|
| | C (%) | H (%) | N (%) |
| Calcd.: | 55.15; | 4.24; | 16.08 |
| Found: | 55.08; | 4.14; | 15.95 |

H-NMR(90 MHz,CDCl₃)δ: 1.43(3H,t), 3.13(3H,s), 3.30(2H,q), 3.83(3H,s), 5.67(2H,s), 7.07–7.63(7H,m), 7.93–8.07(1H,m) IR(Nujol)cm⁻¹:2750, 1680, 1590, 1510, 1445, 1425, 1330, 1320, 1235, 1170, 755

WORKING EXAMPLE 48

2-Ethylthio-4-methylthio-1-[[2'-(1H-tetrazol-5-yl)biphenyl-4-yl]methyl]thieno[3,4-d]imdidazole-6-carboxylic acid The title compound was obtained as colorless needles in 29% yield by the same procedure as in Working Example 2. m.p. 176°–178° C. (d)

| Elemental Analysis for C₂₃H₂₀N₆O₂S₃.0.5H₂O: | | | |
|---|---|---|---|
| | C (%) | H (%) | N (%) |
| Calcd.: | 53.37; | 4.09; | 16.23 |
| Found: | 53.67; | 3.84; | 16.52 |

¹H-NMR(90 MHz,CDCl₃)δ: 1.33(3H,t), 2.67(3H,s), 3.27(2H,q), 5.67(2H,s), 7.07(4H,s), 7.43–7.73(4H,m), IR(Nujol)cm⁻¹:1630, 1575, 1500, 1450, 1320, 1165, 755

WORKING EXAMPLE 49

Methyl 2-Isopropoxy-4-methyl-1-[[2'-(1H-tetrazol-5-yl)biphenyl-4-yl]methyl]thieno[3,4-d]imidazole-6-carboxylate

49a) Methyl 2-Isopropoxy-1-[(2',-cyanobiphenyl-4yl)methyl]-4-methylthieno[3,4-d]imidazole-6-carboxylate The title compound was obtained as colorless crystals in 45% yield by the same procedure as in Working Example 23c) starting from methyl 1-[(2'-cyanobiphenyl-4-yl)methyl]-2-ethylsulfinyl-4-methylthieno[3,4-d]imidazole-6-carboxylate.
¹H-NMR(200 MHz,CDCl₃)δ: 1.39(6H,d), 2.56(3H,s), 3.81(3H,s), 5.25–5.40(1H,m), 5.62(2H,s), 7.35–7.51(6H,m), 7.59–7.67 (1H,m), 7.73–7.77 (1H,m)

49b) Methyl 2-Isopropoxy-4-methyl-1-[2'-(1H-tetrazol-5-yl)biphenyl-4-yl]methyl]thieno[3,4-d]imidazole-6-carboxylate The title compound was obtained as pale yellow crystals in 48% yield by the same procedure as in Working Example 23d). m.p. 170°–173° C. (d)

| Elemental Analysis for C₂₅H₂₄N₆O₃S.0.5H₂O: | | | |
|---|---|---|---|
| | C (%) | H (%) | N (%) |
| Calcd.: | 60.35; | 5.06; | 16.89 |
| Found: | 60.13; | 5.02; | 16.93 |

¹H-NMR(200 MHz,CDCl₃)δ: 1.39(6H,d), 2.52(3H,s), 3.80(3H,s), 5.21–5.34(1H,m), 5.58(2H,s), 7.16(2H,d), 7.31(2H,d), 7.34–7.41(1H,m), 7.50–7.63(2H,m), 8.17–8.22(1H,m) IR(KBr)cm⁻¹:1690, 1570, 1530, 1440, 1380, 1370, 1330, 1320, 1240, 1100, 755

WORKING EXAMPLE 50

2-Isopropoxy-4-methyl-1-[2'-(1H-tetrazol-5-yl)biphenyl-4-yl]methyl]thieno[3,4-d]imidazole-6-carboxylic acid The title compound was obtained as colorless crystals in 46% yield by the same procedure as in Working Example 14. m.p. 184°–188° C. (d)

| Elemental Analysis for $C_{24}H_{22}N_6O_3S \cdot H_2O$: | | | |
|---|---|---|---|
| | C (%) | H (%) | N (%) |
| Calcd.: | 59.49; | 4.99; | 17.34 |
| Found: | 59.19; | 4.68; | 17.21 |

$^1$H-NMR(200 MHz,DMSO-$d_6$)δ: 1.27(6H,d), 2.38(3H,s), 5.04– 5.17(1H,m), 5.70(2H,s), 7.01(2H,d), 7.08(2H,d), 7.23– 7.36(3H,m), 7.48–7.53(1H,m) IR(KBr)cm$^{-1}$:1620, 1570, 1540, 1450, 1445, 1420, 1410, 1380, 1330, 1250, 750

WORKING EXAMPLE 51

Methyl 2-Trifluoromethyl-4-methyl-1-[[2'-(1H-tetrazol-5-yl)biphenyl-4-yl]methyl]thieno[3,4-d]imidazole-6carboxylate

51a) Methyl 4-Methyl-2-trifluoromethylthieno[3,4d]imidazole-6-carboxylate

The title compound was obtained as colorless plates in 55% yield by the same procedure as in Working Example 43a ). m.p. 192°–193° C.

| Elemental Analysis for $C_9H_7F_3N_2O_2S$: | | | |
|---|---|---|---|
| | C (%) | H (%) | N (%) |
| Calcd.: | 40.91; | 2.67; | 10.60 |
| Found: | 40.80; | 2.63; | 10.55 |

$^1$H-NMR(200 MHz, CDCl$_3$)δ: 2.74(3H,s), 3.92(3H,s), 10.1(1H,brs) IR(KBr)cm$^{-1}$:1700, 1620, 1560, 1435, 1370, 1345, 1290, 1220, 1180, 970, 755, 730

51b) Methyl 2-Trifluoromethyl-4-methyl-1-[[2'-(1H-tetrazol-5-yl)biphenyl-4-yl]methyl]thieno[3,4-d]imidazole-6-carboxylate The title compound was obtained as colorless needles in 46% yield by the same procedure as in Working Example 1. m.p. 229°–230° C. (d)

| Elemental Analysis for $C_{23}H_{17}F_3N_6O_2S$: | | | |
|---|---|---|---|
| | C (%) | H (%) | N (%) |
| Calcd.: | 55.42; | 3.44; | 16.86 |
| Found: | 55.36; | 3.51; | 17.13 |

$^1$H-NMR(200 MHz,CDCl$_3$)δ: 2.75(3H,s), 3.81(3H,s), 5.96(2H,s), 7.13(2H,d), 7.21(2H,d), 7.39–7.44(1H,m), 7.51–7.63(2H,m), 8.22–8.26(1H,m) IR(KBr)cm$^{-1}$:1700, 1560, 1450, 1415, 1290, 1250, 1195, 1140, 1125, 755

WORKING EXAMPLE 52

2-Trifluoromethyl-4-methyl-1-[[2'-(1H-tetrazol-5-yl)biphenyl]methyl]thieno[3,4-d]imidazole-6-carboxylic acid The title compound was obtained as colorless needles in 21% yield by the same procedure as in Working Example 14. m.p. 226°–228° C. (d)

| Elemental Analysis for $C_{22}H_{15}F_3N_6O_2S$: | | | |
|---|---|---|---|
| | C (%) | H (%) | N (%) |
| Calcd.: | 54.54; | 3.12; | 17.35 |
| Found: | 54.48; | 2.99; | 17.40 |

$^1$H-NMR(200 MHz,DMSO-$d_6$)δ: 2.69(3H,s), 5.94(2H,s), 6.98(2H,d), 7.05(2H,d), 7.50–7.71(4H,m) IR(KBr)cm$^{-1}$:1645, 1550, 1200, 1145, 760, 750

EXPERIMENTAL EXAMPLE 1

Inhibitory Effect of Binding of Angiotensin-II to Angiotensin Receptor

[Method]

An experiment of inhibition on the binding of angiotensin II (A-II) receptor was conducted by modifying the method of Douglas et al. [Endocrinology, 102, 685–696 (1978)]. An A-II receptor membrane fraction was prepared from bovine adrenal cortex.

The compound of the present invention ($10^{-6}$M or $10^{-7}$M) and $^{125}$I-angiotensin II ($^{125}$I-A-II) (1.85 kBq/50 μl) were added to the receptor membrane fraction, and the mixture was incubated at room temperature for one hour. The receptor-bound and free $^{125}$I-A-II were separated through a filter (Whatman GF/B filter), and the radioactivity of $^{125}$I-A-II bound to the receptor was measured.

[Results]

The results relating to the compounds of the present invention are shown in [Table 1].

EXPERIMENTAL EXAMPLE 2

Inhibitory Effect of the Compound of the Present Invention on Pressor Action of Angiotensin

[Method]

Jcl: SD rats (9 week old, male) were employed. On the day previous to that of the experiment, these animals were applied with cannulation into the femoral artery and vein under anesthesia with pentobarbital Na. The animals were fasted but allowed to access freely to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of angiotensin II (A-II) (100 ng/kg) as the control was measured. The drugs were orally administered, then, at each point of the measurement, A-II was administered intravenously, and the pressor action was similarly measured. By comparing the pressor action before and after administration of the drug, the percent inhibition by the drug on A-II-induced pressor action was evaluated.

[Results]

The results relating to the compounds of the present invention are shown in Table 1.

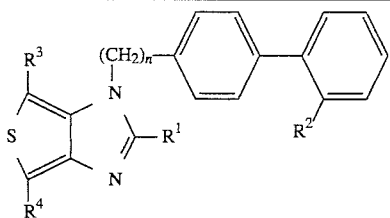

| Working Example | R¹ | R² | R³ | R⁴ | Radioreceptor Assay 1 × $10^{-7}$ M | 1 × $10^{-6}$ M | Pressor Response 1 mg/kg (p.o.) |
|---|---|---|---|---|---|---|---|
| 1 | SEt | Tet | COOMe | Me | 68 | 91 | +[a] |
| 2 | SEt | Tet | COOH | Me | 18 | 64 | +++ |
| 5 | SEt | Tet | COOCH₂OC$^t$Bu | Me | 59 | 89 | +++ |
| 6 | SEt | Tet | COOCHOCO—⟨H⟩ <br> \|<br>Me | Me | 46 | 84 | +++ |
| 7 | SMe | Tet | COOMe | Me | 55 | 77 | + |
| 15 | SMe | Tet | COOH | Me | 14 | 50 | +++ |
| 17 | SiPr | Tet | COOH | Me | 26 | 64 | +++ |
| 18 | SBu | Tet | COOH | Me | 33 | 66 | + |
| 22 | SEt | Tet | COOH | H | 45 | 84 | ++ |
| 28 | OMe | Tet | COOH | Me | 19 | 65 | +++ |
| 29 | OEt | Tet | COOH | Me | 39 | 67 | NT[b] |
| 30 | OPr | Tet | COOH | Me | 33 | 72 | NT |
| 31 | NHEt | Tet | COOH | Me | 26 | 75 | NT |
| 36 | OMe | Tet | COOCH₂OCCH₃ | Me | 73 | 92 | +++ |

[a] +++ ≥ 70% > ++ ≥ 50% > + ≥ 30% > −
[b] N.T. = not tested

What is claimed is:

1. A compound of the formula:

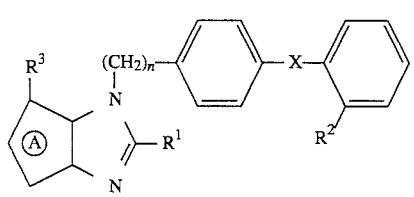

wherein

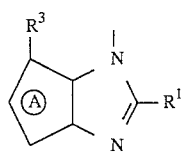

is

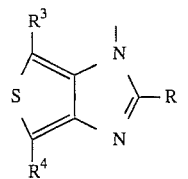

R¹ is hydrogen or a hydrocarbon residue which may be bonded to the imidazole ring through —O—, —S(O)m— or —N($R^5$)— wherein m is O 1 or 2 and $R^5$ represents hydrogen or $C_{1-4}$ alkyl, wherein the hydrobargon residue is selected from the group consisting of $C_{1-8}$ alkyl, $C_{2-8}$ alkenyl, $C_{2-8}$ alkynyl, $C_{3-6}$ cycloalkyl, phenyl-$C_{1-4}$ alkyl and phenyl, in which the $C_{1-8}$ alkyl, $C_{2-8}$ alkenyl, $C_{2-8}$ alkynyl and $C_{3-6}$ cycloalkyl groups are unsubstituted or substituted with hydroxyl amino methylamino, halogen, $C_{1-4}$ alkylthio or $C_{1-4}$ alkoxy, and the phenyl-$C_{1-4}$ alkyl and phenyl groups are unsubstituted or substituted with halogen, nitro, $C_{1-4}$ alkoxy and $C_{1-4}$ alkyl on the benzene moiety, $R^2$ is 1H-tetrazol-5-yl, $R^3$ is a group of the formula: —CO—D' wherein D' is hydoxyl, or 1—C($_{1-6}$ alkoxy unsubstituted or substituted with $C_{2-6}$ alkanoyloxy or alkoxycarbonyloxy on the alkyl moiety, $R^4$ is hydrogen, halogen, $C_{1-4}$ alkyl, $C_{1-4}$ alkoxy, or amino unsubstituted or substituted by $C_{1-4}$ alkyl, X is a chemical bond, $C_{1-4}$ alkylene wherein the atomic length between the phenylene group and the phenyl group is two or less, —C(=O)—, —O—, —S—, —NH—, —C(=O)—NH—, —O—$CH_2$—, —S—$CH_2$— or —CH=CH—, n is 1 or 2, or a pharmaceutically acceptable salt thereof.

2. A compound according to claim 1, wherein $R^1$ is $C_{1-4}$ alkyl which is bonded to the imidazole ring through —O— or —S—.

3. A compound according to claim 1, which is a compound of the formula (I—1):

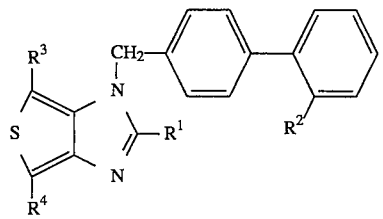

(I-1)

$R^1$ is $C_{1-6}$ alkyl which may be bonded to the imidazole ring through —O—, —S(O)m—, or —N($R^5$)— wherein m is O, 1 or 2 and $R^5$ represents hydrogen or $C_{1-4}$ alkyl, $R^2$ is H-tetrazol-5-yl, $R^3$ is a group of the formula: —CO—D' wherein D' is hydoxyl, or ($C_{1-4}$) is alkoxy unsubstituted or substituted with $C_{2-6}$ alkanoyloxy or 1—C($_{1-6}$) alkoxycarbonyloxy on the alkyl moiety, $R_4$ is hydrogen, halogen, $C_{1-4}$ alkyl, $C_{1-4}$ alkoxy, or amino unsubstituted or substituted by $C_{1-4}$ alkyl, or a pharmaceutically acceptable salt thereof.

4. A compound according to claim 1, wherein X is a chemical bond between the phenylene group and the phenyl group.

5. A compound according to claim 1, wherein n is 1.

6. A compound according to claim 1, which is 2-ethylthio-4-methyl-1-[[ 2'-(1H-tetrazol-5-yl)biphenyl-4yl] methyl]thieno[3,4-d]imidazole-6-carboxylic acid.

7. A compound according to claim 1, which is acetoxymethyl 2-methoxy-4-methyl-1-[[2'-(1H-tetrazol-5-yl) biphenyl-4-yl]methyl]thieno[3,4-d]imidazole-6carboxylate.

8. A compound according to claim 1, which is 2-methoxy-4-methyl-1-[[ 2'-(1H-tetrazol-5-yl)biphenyl-4yl] methyl] thieno[3,4-d]imidazole-6-carboxylic acid.

9. A compound according to claim 1, which is 2-ethoxy-4-methyl-1-[[ 2'-(1H-tetrazol-5-yl)biphenyl-4yl] methyl] thieno[3,4-d]imidazole-6-carboxylic acid.

10. A compound according to claim 1, which is 2-propoxy-4-methyl-1-[[ 2'-(1H-tetrazol-5-yl)biphenyl-4yl] methyl]thieno[3,4-d]imidazole-6-carboxylic acid.

11. A compound according to claim 1, wherein $R^4$ is hydrogen.

12. A compound according to claim 1, wherein D' is hydroxyl or ($C_{1-4}$) alkoxy.

13. A pharmaceutical composition for antagonizing angiotensin II which comprises a therapeutically effective amount of a compound according to claim 1 or a pharmaceutically acceptable salt thereof in admixture with a pharmaceutical acceptable carrier, excipient or diluent.

14. A method for antagonizing angiotensin II in a mammal which comprises administering a therapeutically effective amount of a compound according to claim 1 or a pharmaceutically acceptable salt thereof.

15. A compound according to claim 3, wherein m is 0 and $R^5$ is hydrogen.

16. A compound according to claim 3, wherein D' is hydroxyl or ($C_{1-4}$) alkoxy.

17. A compound according to claim 3 in which $R^4$ is hydrogen, ($C_{1-4}$) alkyl, or halogen.

18. A compound according to claims 3, in which $R^4$ is hydrogen.

19. A pharmaceutical composition for providing an antagonizing angiotensin II which comprises a therapeutically effective amount of a compound according to claim 3 or a pharmaceutically acceptable salt thereof in admixture with a pharmaceutically acceptable carrier, excipient or diluent therefor.

20. A method for providing an antagonizing angiotensin II in a mammal which comprises administering to said mammal a therapeutically effective amount of a compound of claim 3 or a pharmaceutically acceptable salt thereof.

* * * * *

UNITED STATES PATENT AND TRADEMARK OFFICE
CERTIFICATE OF CORRECTION

PATENT NO. : 5,463,073
DATED : October 31, 1995
INVENTOR(S) : Takehiko et al

It is certified that error appears in the above-indentified patent and that said Letters Patent is hereby corrected as shown below:

Column 63, line 1, change "m is 0 1 or 2" to --m is 0, 1 or 2--;

Column 63, line 8, change "hydroxyl amino methylamino" to --hydroxyl, amino, methylamino--;

Column 63, line 15, change "1-C($_{1-6}$ alkoxy" to --1-($C_{1-6}$) alkoxy--;

UNITED STATES PATENT AND TRADEMARK OFFICE
CERTIFICATE OF CORRECTION

PATENT NO. : 5,463,073
DATED : October 31, 1995
INVENTOR(S) : Takehiko et al

It is certified that error appears in the above-indentified patent and that said Letters Patent is hereby corrected as shown below:

Column 63, line 49, change "$(C_{1-4})$ is alkoxy" to --$C_{1-4}$ alkoxy--.

Column 63, lines 50-51, change "1-C$(_{1-6})$ alkoxycarbonyloxy" to --1-$(C_{1-6})$ alkoxycarbonyloxy--.

Signed and Sealed this

Twenty-third Day of July, 1996

BRUCE LEHMAN

Attest:

Attesting Officer    Commissioner of Patents and Trademarks